United States Patent
Tassone et al.

(10) Patent No.: US 10,127,838 B2
(45) Date of Patent: Nov. 13, 2018

(54) SURGICAL SIMULATION SYSTEMS, METHODS, AND COMPOSITIONS

(71) Applicants: Cecilie Tassone, Chicago, IL (US); Alexandre Derevianko, Sharon, MA (US); John Welin, Oak Park, IL (US); Henry Africano, Chicago, IL (US); Georgia Papavasiliou, Chicago, IL (US); Yusheng He, Buffalo Grove, IL (US); Sabina Tassone, Chicago, IL (US)

(72) Inventors: Cecilie Tassone, Chicago, IL (US); Alexandre Derevianko, Sharon, MA (US); John Welin, Oak Park, IL (US); Henry Africano, Chicago, IL (US); Georgia Papavasiliou, Chicago, IL (US); Yusheng He, Buffalo Grove, IL (US); Sabina Tassone, Chicago, IL (US)

(73) Assignee: PraxiCut, LLC, Chicago, IL (US)

( * ) Notice: Subject to any disclaimer, the term of this patent is extended or adjusted under 35 U.S.C. 154(b) by 0 days.

(21) Appl. No.: 15/793,240

(22) Filed: Oct. 25, 2017

(65) Prior Publication Data

US 2018/0144662 A1    May 24, 2018

Related U.S. Application Data

(60) Provisional application No. 62/501,946, filed on May 5, 2017, provisional application No. 62/465,744, filed
(Continued)

(51) Int. Cl.
*G09B 23/28* (2006.01)
*G09B 23/30* (2006.01)
(Continued)

(52) U.S. Cl.
CPC ............ *G09B 23/303* (2013.01); *A61B 34/10* (2016.02); *A61B 34/25* (2016.02); *G09B 23/306* (2013.01);
(Continued)

(58) Field of Classification Search
USPC .................................. 434/262, 267, 268, 272
See application file for complete search history.

(56) References Cited

U.S. PATENT DOCUMENTS

| 3,921,311 A | 11/1975 | Beasley et al. |
| 3,999,309 A | 12/1976 | Gonzalez |

(Continued)

FOREIGN PATENT DOCUMENTS

| CN | 203338651 U | 12/2013 |
| EP | 2772897 B1 | 5/2016 |
| WO | 9321619 A1 | 10/1993 |

OTHER PUBLICATIONS

Laerdal Medical. "An easy to use advanced patient simulator," <https://www.laerdal.com/us/SimMan3G>, SimMan® 3G, Copyright 2018.
(Continued)

*Primary Examiner* — Kurt Fernstrom
(74) *Attorney, Agent, or Firm* — Ashley Sloat

(57) ABSTRACT

A synthetic surgical simulation system includes an anatomical structure comprising a hydrogel and at least 60% water and a tubular structure that is configured to at least partially vaporize, seal, and/or cut in response to an application of energy emitted by an electrosurgical tool. Some exemplary tools are a high-frequency alternating and direct current electrosurgical tool, a high frequency sound wave electrosurgical tool, or an argon beam coagulator. In some embodiments, the system also includes connective tissue. In further embodiments, the connective tissue couples a first anatomi-
(Continued)

cal structure and a second anatomical structure. In some embodiments, the tubular structure is at least partially embedded in one or more of the first anatomical structure, the second anatomical structure, and the connective tissue. In some embodiments, one or more of the connective tissue, the anatomical structure, the first anatomical structure, the second anatomical structure, and the tubular structure comprise poly(ethylene glycol)-diacrylate.

20 Claims, 23 Drawing Sheets

Related U.S. Application Data on Mar. 1, 2017, provisional application No. 62/425,322, filed on Nov. 22, 2016.

(51) Int. Cl.
  *A61B 34/10* (2016.01)
  *A61B 34/00* (2016.01)
  *A61B 34/20* (2016.01)
  *A61B 34/30* (2016.01)
  *A61B 90/00* (2016.01)

(52) U.S. Cl.
  CPC .............. *A61B 34/20* (2016.02); *A61B 34/30* (2016.02); *A61B 34/76* (2016.02); *A61B 90/361* (2016.02)

(56) References Cited

U.S. PATENT DOCUMENTS

| | | | |
|---|---|---|---|
| 4,850,876 A | | 7/1989 | Lutaenko et al. |
| 4,938,696 A | | 7/1990 | Foster et al. |
| 5,112,228 A | | 5/1992 | Zouras |
| 5,149,270 A | | 9/1992 | McKeown |
| 5,403,191 A | | 4/1995 | Tuason |
| 5,518,406 A | | 5/1996 | Waters |
| 5,518,407 A | | 5/1996 | Greenfield et al. |
| 5,620,326 A | * | 4/1997 | Younker ............... G09B 23/28 434/268 |
| 5,857,626 A | | 1/1999 | Hsu |
| 5,951,301 A | | 9/1999 | Younker |
| 6,336,812 B1 | | 1/2002 | Cooper et al. |
| 6,474,993 B1 | * | 11/2002 | Grund ............... A61L 27/20 434/262 |
| 6,780,016 B1 | | 8/2004 | Toly |
| 7,272,766 B2 | | 9/2007 | Sakezles |
| 7,427,199 B2 | * | 9/2008 | Sakezles ............... G09B 23/28 434/267 |
| 7,507,092 B2 | | 3/2009 | Sakezles |
| 7,699,615 B2 | | 4/2010 | Sakezles |
| 7,850,454 B2 | | 12/2010 | Toly |
| 7,857,626 B2 | | 12/2010 | Toly |
| 8,297,982 B2 | | 10/2012 | Park et al. |
| 8,403,675 B2 | | 3/2013 | Stoianovici et al. |
| 8,403,676 B2 | | 3/2013 | Frassica et al. |
| 8,425,234 B2 | | 4/2013 | Sakezles |
| 8,469,713 B2 | | 6/2013 | Fedotov et al. |
| 8,469,716 B2 | | 6/2013 | Fedotov |
| 8,702,431 B2 | * | 4/2014 | Ikeno ............... G09B 23/303 434/267 |
| 8,801,438 B2 | * | 8/2014 | Sakezles ............... G09B 23/34 434/274 |
| 8,870,576 B2 | * | 10/2014 | Millon ............... B29C 39/003 434/267 |
| 8,920,176 B1 | | 12/2014 | Yang |
| 2005/0214727 A1 | | 9/2005 | Stoianovici et al. |
| 2008/0076101 A1 | * | 3/2008 | Hyde ............... G09B 23/30 434/272 |
| 2008/0138778 A1 | * | 6/2008 | Eggert ............... G06F 19/3437 434/262 |
| 2010/0055184 A1 | * | 3/2010 | Zeitels ............... A61K 31/00 424/484 |
| 2012/0045742 A1 | * | 2/2012 | Meglan ............... G09B 23/28 434/268 |
| 2012/0288839 A1 | * | 11/2012 | Crabtree ............... B65D 75/008 434/267 |
| 2013/0059280 A1 | * | 3/2013 | Haverich ............... C12N 5/00 434/272 |
| 2013/0177890 A1 | | 7/2013 | Sakezles |
| 2014/0011172 A1 | | 1/2014 | Lowe |
| 2014/0248596 A1 | | 9/2014 | Hart et al. |
| 2014/0272879 A1 | | 9/2014 | Shim |
| 2014/0329217 A1 | | 11/2014 | Barsness et al. |
| 2015/0086955 A1 | * | 3/2015 | Poniatowski ......... G09B 23/28 434/267 |

OTHER PUBLICATIONS

Simulab Corporation. "Surgical Trainer for Chest Tube Insertion, Cricothyroidomy (or Cricothyrotomy), Needle Decompression, Tracheostomy, Pericardiocentesis and Diagnostic Peritoneal," <http://www.simulab.com/traumaman-procedures>, Copyright 2017.
"3-Dmed® Learning Through Simulation," <http://www.pentaint.net/catalogos/3dmed_catalogo.pdf>.
Laboratoire De Systemes Robotiques LSRO. "Surgical Simulators with Haptic Feedback," <http://lsro.epfl.ch/simulators>.
CAE Healthcare. "Abdominal Aortic Aneurysm Ultrasound Training Model," <http://www.bluephantom.com/product/Abdominal-Aortic-Aneurysm-Ultrasound-Training-Model.aspx?cid=455>, Copyright 2015.
LifeLike BioTissue. "Abdominal Aortic Aneurysm (AAA) Abdomen Simulator," <http://lifelikebiotissue.com/shop/vascular-surgery/abdominal-aortic-aneurysm-aaa-abdomen-simulator>, Copyright 2018.
Kyoto Kagaku Co., Ltd. "Ultrasound Examination Training Model ABDFAN," <https://www.kyotokagaku.com/products/detail03/us-1b.html>, Copyright 1999-2012.
Wellcome Trust. "Surgery at the Science Museum: A Retro Revival," <http://blog.wellcome.ac.uk/2011/08/24/surgery-at-the-science-museum/> Aug. 24, 2011.
Computerized Imaging Reference Systems, Inc.: A Castleray Company. "Triple Modality 3D Abdonimal Phantom," <http://www.cirsinc.com/products/all/65/triple-modality-3d-abdominal-phantom/>, CIRS Tissue Simulation & Phantom Technology, Copyright 2018.
Simulab Corporation. <http://www.simulab.com/>, Copyright 2017.
Rosen, K., abstract of article entitled "The history of medical simulation," Journal of Critical Care, Jun. 2008, vol. 23, Issue 2, pp. 157-166.
North American Rescue and Operative Experience, Inc. "Combat Trauma Simulators," <https://www.narescue.com/media/custom/upload/File-1443550289.pdf>.
Alibaba.com. "Training Model for Open and Close of Abdominal Cavity," <https://www.alibaba.com/product-detail/Training-Model-for-Open-and-Close_755867090.html>, Copyright 1999-2018.

* cited by examiner

SURGICAL SIMULATION SYSTEMS, METHODS, AND COMPOSITIONS

CROSS REFERENCE TO RELATED APPLICATIONS

This application claims priority benefits to U.S. provisional patent application Ser. No. 62/425,322, titled "SURGICAL SIMULATION SYSTEMS, METHODS, AND COMPOSITIONS", filed Nov. 22, 2016, and U.S. provisional patent application Ser. No. 62/465,744, titled "SURGICAL SIMULATION METHODS AND COMPOSITIONS", filed Mar. 1, 2017, and U.S. provisional patent application Ser. No. 62/501,946, titled "SURGICAL SIMULATION SYSTEMS, METHODS, AND COMPOSITIONS", filed May 5, 2017, all of which are herein incorporated by reference in its entirety.

TECHNICAL FIELD

This disclosure relates generally to the field of medical training, and more specifically to the field of medical procedure simulation. Described herein are surgical simulation systems, methods, and compositions.

BACKGROUND

Iatrogenic disease, illness caused by treatment by a physician, is the third leading cause of death in the U.S. following heart disease and cancer, respectively. Conservative estimates indicate that over 250,000 people die every year in the U.S. due to iatrogenic disease. The high incidence of iatrogenic disease in the U.S. is a result, in part, of the inadequacy of effective tools for surgical training and training of medical personnel entering the workforce. As a result, residents are released from residency with inadequate experience and are not prepared for entering the physician workforce. These findings are demonstrated by the lack of general surgeons in the physician workforce and the excessive adverse events in surgery that result in disability and/or death. The population continues to grow steadily yet the current supply of general surgeons do not meet the demand. With projected aging population and increased healthcare needs, the supply is also likely unable to meet the demands of 2025. Population projections are expected to continue to increase by 1% every year. Unfortunately, over the last 25 years the number of general surgeons has been steadily decreasing about 1% every year for a total of 26% less general surgeons between 1981 and 2005 (Lynge D C, et al. "A longitudinal analysis of the general surgery workforce in the United States, 1981-2005." *Arch Surg* 2008; 143:345-50.).

Surgical adverse events have several associated costs including: economic loss, malpractice lawsuits against health care systems, community and patient trust in those health care systems, decreased satisfaction for both health care providers and patients. According to a 2013 Institute of Medicine report (Best Care at Lower Cost: The Path to Continuously Learning in America), an estimated $2.6 trillion is spent in healthcare annually. Unfortunately, $750 billion of that is spent on inefficient and wasteful healthcare. In other words, one-third of health care expenditures are wasted. Extrapolating for the 60% of medical errors that occur in the operating room, $450 billion is lost annually due to operative errors.

In general, 60% of all adverse events are attributed to surgical errors (E. de Vries, et. al. "The incidence and nature of in-hospital adverse events: a systematic review." *Qual Saf Health Care*, 2008; 17(3): 216-223.). Specifically, the causes of errors include poor surgical technique (33%), inattention to detail (15%), judgement error (12%) and an incomplete understanding of the procedure (12%) (P. J. Fabri, J. L. Zayas-Castro. "Human error, not communication and systems, underlies surgical complications." *Surgery*, 2008; 144: 557-563.). All of these errors occurring during surgery are preventable and, at least in part, are due to the inability of residents to practice and receive feedback on their surgical technique before operating on patients.

Due to the lack of adequate preparation in general surgery residency, a dearth of general surgeons has been created due to the increase in popularity of surgical subspecialization. Over 80% of general surgery residents choose to join fellowship programs following residency (Jancin B. "Surgical fellowship directors: General surgery trainees arrive ill prepared." *The Oncology Report*. May 1, 2013.). Further, investigations have revealed that 25% of senior surgery residents feel inadequately prepared for independent practice (Bucholz E M, et al. "Our trainees' confidence: Results from a national survey of 4136 U.S. general surgery residents." *Arch Surg*. 2011; 146(8):907-914.).

Current systems and methods of training general surgeons include animal and cadaver surgeries as well as other simulators (Beyer-Berjot L, et al. "Advanced training in laparoscopic abdominal surgery: a systematic review." *Surgery*, 2014; 156(3):676-88; Sharma M, et al. "Basic laparoscopic skills training using fresh frozen cadaver: a randomized controlled trial." *Am J Surg*, 2013; 206(1):23-31.). While currently available systems and methods do simulate operations or procedures to varying degrees, these surgical simulators are lacking in several areas. For example, the materials used in current products are not compatible with electrosurgical instruments and lack adequate tactile sensation and anatomy. Currently available products do not allow for practice of modern laparoscopic procedures with electrosurgical tools because the materials are not compatible with the electrosurgical instruments. The materials in currently available products either cannot be safely used with electrosurgical instruments or do not give the proper response when energy is applied to the materials. Further for example, the anatomy of the currently available products differs as compared to human anatomy. In many cases, the shape, color, and/or size of the synthetic tissues or anatomy is not realistic or true to analogous human tissues. Additionally, many currently available products do not have connective tissues to house vessels. In fact, many of the abdominal organs available do not even include an integrated vascular system. A method of physically connecting each of the organs and tissues to one another is imperative to simulating a surgical procedure.

Better training tools are needed to adequately prepare future general surgeons and increase the chance that surgeons remain in general practice to meet supply needs. Current approaches limit the quality and functionality of a simulator for abdominal surgeries, a common procedure for general surgeons, because they lack the innovative modular approach to solving the problem. Each area of the body includes many different types of tissues that are physically connected to one another; this is not seen in current products. Thus, the current landscape of abdominal surgical simulation products lacks innovative materials and integration of those materials to one another. More sophisticated simulation tools are desperately needed to appropriately address these issues.

SUMMARY

The present invention is contemplated to comprise a synthetic surgical simulation system comprising an anatomical structure configured to at least partially vaporize, seal, and cut in response to an application of energy emitted by an electrosurgical tool, where the anatomical structure comprises a hydrogel and at least 60% water and a tubular structure at least partially embedded in the anatomical structure. In some embodiments, the anatomical structure and/or tubular structure includes or is formed of a thermoset polymer. In some embodiments, the anatomical structure is a liver. In further embodiments, the tubular structure comprises one or more of: a synthetic superior vena cava, a synthetic inferior vena cava, a synthetic left hepatic vein, a synthetic middle hepatic vein, a synthetic right hepatic vein, a synthetic hepatic artery, a synthetic hepatic portal vein, and a synthetic common bile duct.

In still further embodiments, the tubular structure is a network where the network extends from the anatomical structure and is coupled to a reservoir. In some of the embodiments, the reservoir monitors an amount of blood loss during a medical training session. Additional embodiments of the present invention further comprise a pump coupled to the reservoir, such that the pump pumps a fluid from the reservoir through the network of tubular structures. With some embodiments, the fluid is pumped in a pulsatile manner.

For some embodiments of the present invention, the electrosurgical tool used to apply electrical energy can be selected from a group consisting of: a high-frequency alternating current electrosurgical tool, a high-frequency direct current electrosurgical tool, a high frequency sound wave electrosurgical tool, and an argon beam coagulator. For still further embodiments of the present invention, the appearance of the anatomical structure is based on one or more of: a computerized tomography, a magnetic resonance imaging, and a magnetic resonance elastography scan of a body portion of a patient. In additional embodiments of the present invention, the anatomical structure comprises poly(ethylene glycol)-diacrylate.

Embodiments of the present synthetic surgical simulation system can also comprise a first anatomical structure, a second anatomical structure, and a connective tissue coupling the first anatomical structure to the second anatomical structure. Within contemplated embodiments one or more of the first anatomical structure, the second anatomical structure, and the connective tissue is further configured to at least partially vaporize, seal, and cut in response to an application of energy emitted by an electrosurgical tool and a tubular structure is at least partially embedded in one or more of the first anatomical structure, the second anatomical structure, and the connective tissue. In further embodiments, the tubular structure couples together one or more of the first anatomical structure, the connective tissue, and the second anatomical structure. The system of the present invention, in some embodiments, is designed for the use of an electrosurgical tool selected from a group consisting of a high-frequency alternating and direct current electrosurgical tool, a high frequency sound wave electrosurgical tool, and an argon beam coagulator.

It is contemplated for embodiments of the system of the present invention the first anatomical structure is a liver and the second anatomical structure is a gall bladder. Some embodiments can have a tubular structure that comprises one or more synthetic superior vena cava, synthetic inferior vena cava, synthetic left hepatic vein, synthetic middle hepatic vein, synthetic right hepatic vein, synthetic hepatic artery, synthetic hepatic portal vein, and synthetic common bile duct. A still further embodiment has tubular structures that are a closed network. Some embodiments of the present invention have connective tissue that is one or more synthetic reticulin, adventia, and serosa. Further embodiments comprising a housing configured to house the first anatomical structure, the second anatomical structure, and the connective tissue. Additional embodiments comprise a tubular structure that is a network where the network extends from the housing and is coupled to a reservoir. In certain embodiments the reservoir monitors an amount of blood loss during a medical training session. Other embodiments further comprising a pump coupled to the reservoir, wherein the pump pumps a fluid from the reservoir through the network of tubular structures. With still other embodiments the fluid is pumped in a pulsatile manner.

For embodiments of the present invention the appearance of one or more of the first anatomical structure and the second anatomical structure is based on one or more of a computerized tomography, magnetic resonance imaging, and magnetic resonance elastography scan of a patient. For embodiments within the present invention one or more of the connective tissue, the first anatomical structure, and the second anatomical structure comprise poly(ethylene glycol)-diacrylate.

The present invention also contemplates a method of training a user in surgical techniques comprising utilizing the synthetic surgical simulation system described herein. One particular set of embodiments is where the surgical technique comprises a liver transplant veno-venous bypass. Another set of embodiments is where the surgical technique comprises a splenectomy.

The present invention also encompasses a synthetic surgical simulation system comprising a first anatomical structure, a second anatomical structure, a connective tissue coupling the first anatomical structure to the second anatomical structure. One embodiment contemplates one or more of the first anatomical structure, the second anatomical structure, and the connective tissue to be configured to at least partially vaporize, cut, and seal in response to an application of energy emitted by an electrosurgical tool. The present surgical simulation systems can also comprise a network of tubular structures comprising a first portion at least partially embedded in the first anatomical structure, a second portion at least partially embedded in the second anatomical structure, and a third portion at least partially embedded in the connective tissue. One embodiment contemplates the first portion, the second portion, and the third portion of the network of tubular structures being interconnected to further couple the first anatomical structure, the second anatomical structure, and the connective tissue together.

A further embodiment of the present invention comprises a housing configured to house the first anatomical structure, the second anatomical structure, and the connective tissue. A still further embodiment contemplates a system comprising a fourth portion of the network of tubular structures, wherein the fourth portion is coupled to one or more of the first portion, the second portion, and the third portion, and wherein the fourth portion extends from the housing and is coupled to a reservoir. The reservoir can be configured to monitor an amount of blood loss during a medical training session. An additional embodiment comprises a pump coupled to the reservoir, wherein the pump pumps a fluid from the reservoir through the network of tubular structures. The fluid can be pumped in a pulsatile manner.

The system of the present invention, in some embodiments, is designed for the use of an electrosurgical tool selected from a group consisting of a high-frequency alternating and direct current electrosurgical tool, a high frequency sound wave electrosurgical tool, and an argon beam coagulator.

A further embodiment of the systems of the present invention is where the first anatomical structure is a liver and the second anatomical structure is a gall bladder. In some embodiments, the tubular network comprises one or more of the superior vena cava, the inferior vena cava, the left hepatic vein, the middle hepatic vein, the right hepatic vein, the hepatic artery, the hepatic portal vein, and the common bile duct. The connective tissue can be one or more of the reticulin, adventia, and the serosa.

A still further embodiment of the present system is where the first anatomical structure is a synthetic spleen and the second anatomical structure is a synthetic stomach. The connective tissue can be a synthetic splenogastric ligament. Alternatively, the first anatomical structure is a synthetic spleen and the second anatomical structure is a synthetic pancreas. The connective tissue can be a synthetic splenic-pancreatic ligament. Alternatively, the first anatomical structure is a synthetic spleen and the second anatomical structure is a synthetic colon. The connective tissue can be a synthetic splenocolic ligament.

In some embodiments of the present invention, the first and second anatomical structures each comprise a protrusion and the connective tissue comprises a loop such that the loop is fitted over the protrusion to couple the first and second anatomical structures to the connective tissue. Embodiments of the present invention contemplate the first and second anatomical structures each comprise a hook and the connective tissue comprises an eye such that the hook fastens to the eye to couple the first and second anatomical structures to the connective tissue.

In embodiments of the present invention one or more of the connective tissue, the first anatomical structure, and the second anatomical structure comprise poly(ethylene glycol)-diacrylate.

Further, in embodiments of the present invention appearance of one or more of the first anatomical structure and the second anatomical structure is based on one or more of a computerized tomography, magnetic resonance imaging, and magnetic resonance elastography scan of a patient. In further embodiments, the tortuosity of one or more of the first portion, the second portion, and the third portion is altered to change a complexity of the synthetic surgical simulation system. In some further embodiments of the systems of the present invention when the network of tubular structures comprises n number of tubular structures, n can be increased or decreased to change a complexity of the synthetic surgical simulation system. In still further embodiments of the systems of the present invention one or more of a size, a shape, a hardness, and a stiffness of one or more of: the first anatomical structure and the second anatomical structure is altered to change a complexity of the synthetic surgical simulation system.

The present inventions' embodiments contemplate a network of tubular structures is interconnected via a series of complementary fasteners and that network of tubular structures can be a closed network.

BRIEF DESCRIPTION OF THE DRAWINGS

The above-mentioned aspects, as well as other aspects, features, and advantages of the present technology are described below in connection with various embodiments, with reference made to the accompanying drawings.

Figure 1:
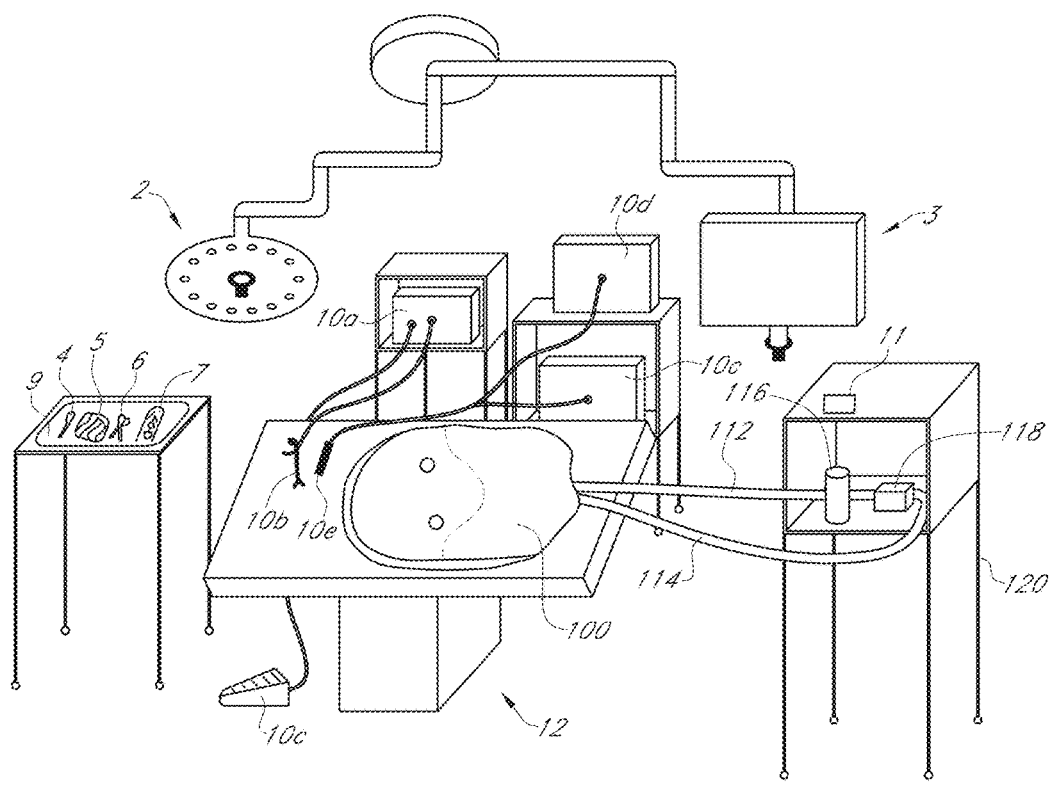
FIG. 1 illustrates a perspective view of one embodiment of a surgical simulation system.

The illustrated embodiments are merely examples and are not intended to limit the disclosure. The schematics are drawn to illustrate features and concepts and are not necessarily drawn to scale.

DETAILED DESCRIPTION

The above mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

As described herein, the system and methods may incorporate human anatomy or anatomy of an animal, for example to practice veterinary surgical procedures. It will be understood by one of skill in the relevant art that any anatomy may be used without departing from the original scope and intent of the present disclosure. The systems and methods described herein may be used to practice a procedure or surgery. Non-limiting example of procedures and surgeries include: splenectomy, open heart surgery, laproscopic procedures, bariatric surgeries, reconstruction surgeries, cholecystectomy, appendectomy, pancreas dissection, distal pancreatic resection, proximal pancreatic resection (also called the Whipple procedure), liver resection, gastric resection, gastrectomy, abdominal wall hernia repair, total nephrectomy, partial nephrectomy, bariatric gastric bypass, bariatric gastric sleeve resection, bowel resection, bowel anastomosis, colectomy, right hemicolectomy, left hemicolectomy, left adrenalectomy, right adrenalectomy, hepaticojejunostomy, esophagectomy, common bile duct exploration, gastric fundoplication for reflux disease (Dor), gastric fundoplication for reflux disease (Tupet), left anterior rectosigmoid resection, rectosigmoid resection, rectosigmoid anastomosis, radical cystectomy, control of bleeding, porta hepatic dissection, Heller myotomy, colonoscopy, endoscopy, hemorrhoidectomy, abdominal aortic aneurism repair, opening and closing of the abdomen, oophrectomy, hysterectomy and salpingectomy, or any other procedure or surgery.

As described herein, a "user" refers to any individual buying, selling, setting-up, using, and/or practicing on or with the systems, methods, and compositions described herein. In non-limiting examples, a user includes a physician, a physician assistant, a surgeon, a lab technician, a resident, a medical school student, a veterinarian, a veterinary school student, a nurse, a nurse practitioner, an emergency medical technician, a teacher, a medical personnel, a student, an administrator, or any individual associated with, capable of using, or responsible for handling medical equipment or systems.

As described herein, an "anatomical structure" refers to any structure capable of being connected to a second structure via connective tissue or a tubular structure. Non-limiting examples of anatomical structures include: teeth, tongue, salivary glands, parotid glands, submandibular glands, sublingual glands, pharynx, esophagus, stomach, small intestine, duodenum, jejunum, ileum, large intestine, colon, liver, gallbladder, pancreas, nasal cavity, larynx, trachea, bronchi, lungs, diaphragm, kidney, ureter, bladder, urethra, ovary, fallopian tube, uterus, vagina, vulva, clitoris, placenta, testes, epididymis, vas deferens, seminal vesicles, prostate, bulbourethral glands, penis, scrotum, pituitary gland, pineal gland, thyroid gland, parathyroid glands, adrenal glands, heart, lymph node, bone marrow, thymus, spleen, brain, cerebral hemisphere, diencephalon, brainstem, midbrain, pons, medulla oblongata, cerebellum, spinal cord, brain ventricle, choroid plexus, nerves, cranial nerves, spinal nerves, eye, cornea, iris, ciliary body, lens, retina, ear, outer ear, earlobe, eardrum, middle ear, ossicles, inner ear, cochlea, vestibule of the ear, semicircular canals, olfactory epithelium, taste buds, mammary glands, or any structure similar in size, shape, and/or color to any organ, gland, or muscle in a human or animal body.

As described herein, a "connective tissue" refers to any structure that connects, supports, binds, or separates one or more anatomical structures and/or tubular structures. Non-limiting examples of connective tissues include cervical vertebrae, thoracic vertebrae, lumbar vertebrae, extra lumbar vertebrae, sacral vertebrae, coccygeal vertebrae, sternum, ribs, skull, cranial bones, occipital bones, parietal bones, frontal bone, temporal bone, sphenoid bone, ethmoid bone, facial bone, nasal bone, maxillae, lacrimal bone, zygomatic bone, palatine bone, inferior nasal concha, vomer, mandible, hyoid bone, middle ears, malleus, incus, stapes, clavicle, scapula, humerus, ulna, radius, carpals, scaphoid bone, lunate bone, triquetrum bone, pisiform bone, trapezium, trapezoid bone, capitate bone, hamate bone, metacarpals, foot or hand proximal phalanges, foot or hand intermediate phalanges, foot or hand distal phalanges, coxal bone, ilium, ischium, pubis, femur, patella, tibia, fibula, tarsus, calcaneus, talus, navicular bone, medial cuneiform bone, intermediate cuneiform bone, lateral cuneiform bone, cuboid bone, metatarsals, sesamoid bones, patella, pisiform bone, fabella, cyamella, rider's bone, fascia, pleural sac, pericardial sac, mesentery, ligaments, tendons, cartilage, omentum, flexures, peritoneum, or any structure similar in size, shape, and/or color in a human or animal body.

As describe herein, a "tubular structure" refers to any structure that transports fluid. Non-limiting examples of tubular structures include an artery, vein, arterioles, venules, capillary, lymphatic vessel, or any structure similar in size, shape, and/or color in a human or animal body.

As described herein, an "electrosurgical tool" refers to any tool used to cut, coagulate, desiccate, seal, vaporize, and/or fulgurate tissue during a real or simulated medical procedure. In some embodiments, an electrosurgical tool uses energy to manipulate the tissue. In one embodiment, an electrosurgical tool employs high frequency ultrasound. In one embodiment, an electrosurgical tool employs high frequency alternating current. In one embodiment, an electrosurgical tool employs direct current through a monopolar electrosurgical instrument. In one embodiment, an electrosurgical tool employs an argon beam coagulator.

As described herein, a "mechanical tool" refers to any tool used to cut, coagulate, seal, and/or fulgurate tissue during a real or simulated medical procedure. Non-limiting example of mechanical tools include conventional mechanical tools (e.g., scalpel, scissors, etc.) and endomechanical instruments (e.g., staplers).

In some embodiments, the system and methods may also be used with surgical robots or other remote surgical procedure apparatuses.

As described herein, "synthetic" refers to a material or structure made in a laboratory. However, any material or structure described herein may include a synthetic polymer, a natural polymer, or a combination of one or more synthetic and natural polymers.

As described herein, "thermoset polymer" or a "thermosetting polymer" refers to a material which is a three dimensional, chemically resistant network, that can also be referred to as a gel or hydrogel, vulcanizate, or cured material. Thermosets are formed when polyfunctional reactants generate three-dimensional network structures via the progression of linear growth, branching, gelation, and post-gelation reactions. The starting monomers generally include at least some reactive functionality greater than two, which will ensure that as the reaction proceeds, the number of chain ends will increase. They will eventually interconnect to produce a gelled network material. This process may be followed by observing the viscosity increase as a function of time or from the percent reaction completed. As the gel begins to form, the soluble fraction decreases and may eventually be eliminated altogether. Generally, the cure is irreversible. Thermoset polymers respond to energy from an electrosurgical tool by burning or decomposing rather than melting and do not reform upon cooling. Non-limiting examples of thermoset polymers include: poly(ethylene glycol)-diacrylate, polyester resins, polyurethanes, polyurea, polyurethane, vulcanized rubber, phenol-formaldehyde resins, duroplast, urea-formaldehyde, melamine resin, diallylphthalate, epoxy resin, epoxy novolac resins, benzoxazines, polyimides, bismaleimides, cyanate esters, polycyanurates, furan resins, silicone resins, and vinyl ester resins. In some embodiments described elsewhere herein, one or more synthetic anatomical structures comprise a thermoset polymer or are formed of, at least in part, a thermoset polymer. In some non-limiting examples, a synthetic spleen and a synthetic liver comprise or are formed of, at least in part, a thermoset polymer.

As described herein, a "thermoplastic polymer" refers to a plastic material that melts or becomes pliable or moldable with the application of heat, for example at a specific temperature. Upon cooling of a thermoplastic polymer, the material reforms. Non-limiting examples of thermoplastic polymers include: acrylic (poly (methyl methacrylate)), acrylonitrile butadiene styrene, nylon, polylactic acid (polylactide), polybenzimidazole, polycarbonate, polyether sulfone, polyoxymethylene, polyetherether ketone, polyetherimide, polyethylene, polyphenylene oxide, polyphenylene sulfide, polypropylene, polystyrene, polyvinyl chloride, and Teflon. In some embodiments, one or more synthetic anatomical structures comprise a thermoplastic polymer. For example, a synthetic liver comprises or is formed of, at least in part, a thermoplastic polymer.

Systems

FIG. 1 illustrates a perspective view of one embodiment of a surgical simulation system 100. The system 100 functions to provide an anatomically correct, mechanical tool and/or electrosurgical tool responsive system for training medical professionals and personnel. The system 100 is used in the medical training field, but can additionally or alternatively be used for any suitable applications, for example veterinary medicine, patient and/or student education, or otherwise.

In some embodiments, a surgical simulation system 100 is configured to be used in an operating room, a laboratory, a training room or facility, an emergency room, a class room, or any other suitable location or room. As shown in FIG. 1, a surgical simulation system 100 may be used in combination with an overhead light 2, one or more monitors 3, one or more surgical tools (e.g., electrosurgical unit 10a, electrosurgical instruments 10b, mechanical surgical instruments such as scalpel 4 and scissors 6), a foot control for one or more electrosurgical tools and/or laparoscopic tools 10c, laparoscopic camera system 10e including light source and audio-visual processing unit 10d, one or more insufflation devices, gauze 5, towels 7, and storage for these tools such as one or more trays 9 and/or carts for the instruments. In some embodiments, a surgical simulation system 100 may be positioned on a table or flat surface 12 to enable users to set-up, adjust, access, practice, or otherwise use the surgical simulation system 100.

In some embodiments, a surgical simulation system 100 includes one or more tubular structures, for example an abdominal aorta 112 and hepatic portal vein 114, for connecting the surgical simulation system 100 to a reservoir 116 and a pump 118, as will be described in further detail elsewhere herein. In one embodiment, the reservoir 116 is positioned within the housing of the system. In another embodiment, the reservoir 116 is positioned externally to the housing, as shown in FIG. 1. The reservoir 116 functions to store fluid 11 that is pumped throughout the system, for example to simulate blood flow through one or more anatomical structures, connective tissues, and/or tubular structures. In some embodiments, the reservoir 116 is positioned on or in a tower, cart, or mobile platform 120 proximate the surgical simulation system 100, as shown in FIG. 1. In some embodiments, the height of the mobile platform 120 is configured to maintain a pressure gradient of a fluid being pumped through the surgical simulation system 100. In one embodiment, the height of the mobile platform 120 is adjustable to maintain, increase, or decrease a pressure gradient of a fluid being pumped through the surgical simulation system 100. In some embodiments, the fluid 11 is pumped from the reservoir 116 through the housing (including one or more anatomical structures, tubular structures, and/or connective tissues) to the pump 118 and then back to the reservoir 116. In other embodiments, the fluid is pumped from the pump 118 through the housing to the reservoir 116 and then back to the pump 118.

Figure 2:
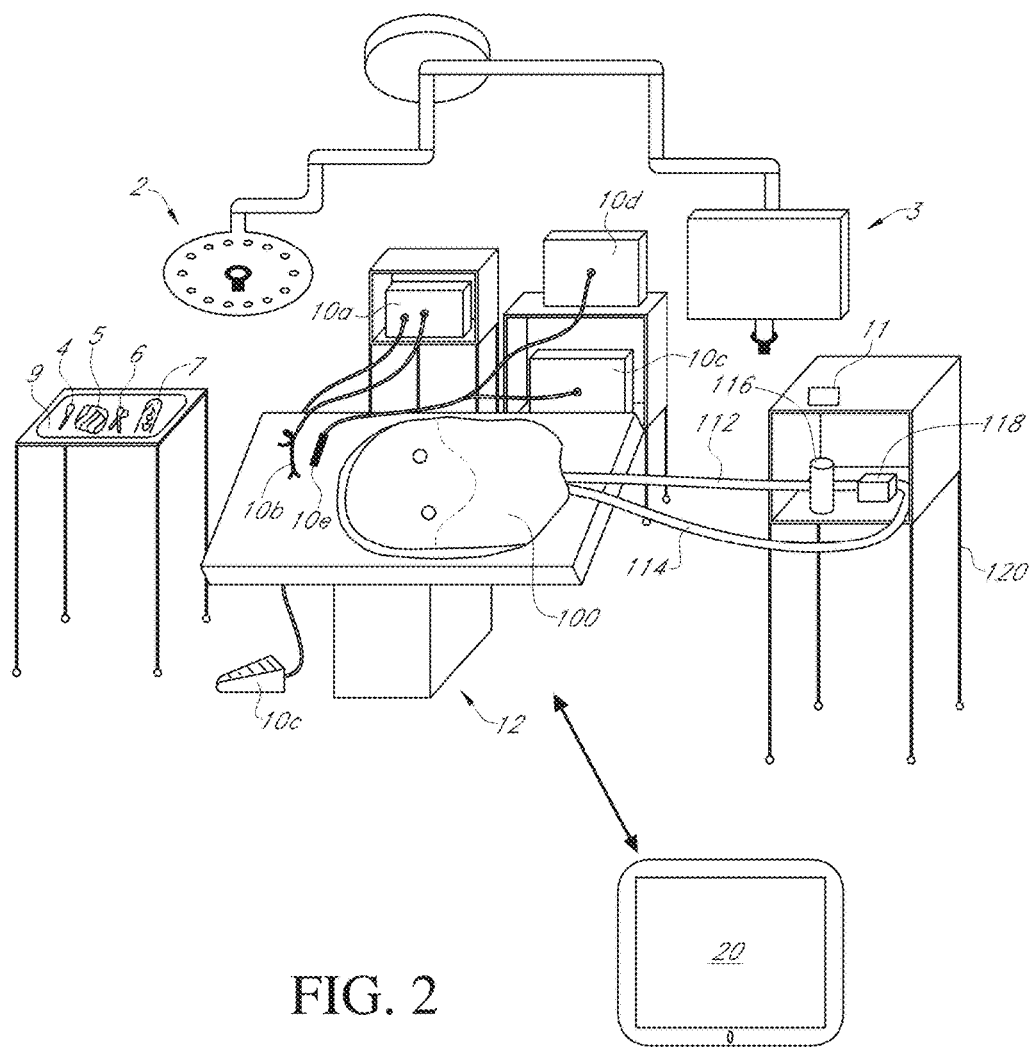
FIG. 2 illustrates a perspective view of another embodiment of a surgical simulation system.

In some embodiments, as shown in FIG. 2, a surgical simulation system 100 includes a computing device 20. The computing device 20 functions to receive data from the surgical simulation system 100 and/or transmit data to the surgical simulation system 100. For example, the computing device 20 may receive data related to a quality or a speed of a performance of a user practicing a technique or surgical procedure using the surgical simulation system 100. Further for example, the system may track an amount of blood loss during the procedure and transmit blood loss data to a computing device 20 communicatively coupled to the system 100. In some embodiments, the system 100 may transmit one or more user parameters (e.g., amount of blood loss, technique quality, speed, accuracy, etc.) to the computing device 20 and the computing device 20 may calculate and/or display a score, a rating, or otherwise assessment of a performance of a user practicing a technique or surgery using the surgical simulation system 100. In one such embodiment, the computing device 20 compares a first user to a second user or a plurality of users, and calculates statistics of the first user's performance relative to the second user or the plurality of users in using the surgical simulation system 100 to practice a technique or surgical procedure.

In one embodiment, the computing device 20 is a stationary computing device, for example a workstation or desktop computer. In another embodiment, the computing device 20 is a mobile computing device, for example a laptop, netbook, notebook, personal digital assistant, mobile phone, tablet, or other mobile device. In another embodiment, the computing device 20 is a wearable computing device, for example a watch, glasses, earpiece, bracelet, necklace, anklet, or other wearable computing device.

In some embodiments, there is bidirectional communication between the surgical simulation system 100 and the computing device 20. In one embodiment, the communication occurs via a wired connection (e.g., IEEE 1394, Thunderbolt, Lightning, DVI, HDMI, Serial, Universal Serial Bus, Parallel, Ethernet, Coaxial, VGA, or PS/2). In another embodiment, the communication occurs via a wireless connection (e.g., Bluetooth, low energy Bluetooth, near-field communication, infrared, WLAN, Wi-Fi, CDMA, LTE, other cellular protocol, other radiofrequency, or another wireless protocol).

In some embodiments, the computing device 20 is a series of components connected via an electronic circuit and wrapped in a chassis including a display, for example a visual display with or without touch-responsive capabilities. Non-limiting examples of components include: one or more processors (e.g., microprocessor, DSP, ASC, programmable logic device), one or more radios (e.g., WLAN, GPS, BlueTooth, etc.), one or more specialized chips and/or sensors (e.g., accelerometer, gyroscope, etc.), and internal storage (e.g., flash drive).

The processor functions to read information from and optionally write information to memory. The processor may be coupled to the memory via one or more buses. The memory may be a computer readable medium that functions to store computer readable instructions for execution by a processor. The computer readable instructions may include software stored in a non-transitory format. The software may include instructions for execution by the processor, the instructions comprising a method of determining a fluid volume, as will be described in further detail elsewhere herein.

In some embodiments, as shown in FIGS. 3-10, a surgical simulation system 100 includes a first anatomical structure; a second anatomical structure; a connective tissue coupling the first anatomical structure to the second anatomical structure; and a tubular structure. In one embodiment, the tubular structure further couples together the first anatomical structure, the connective tissue, and/or the second anatomical structure and/or couples the surgical simulation system 100 to a reservoir 116. In another embodiment, the tubular structure is at least partially embedded in one or more of the first anatomical structure, the second anatomical structure, and the connective tissue.

Figure 3:
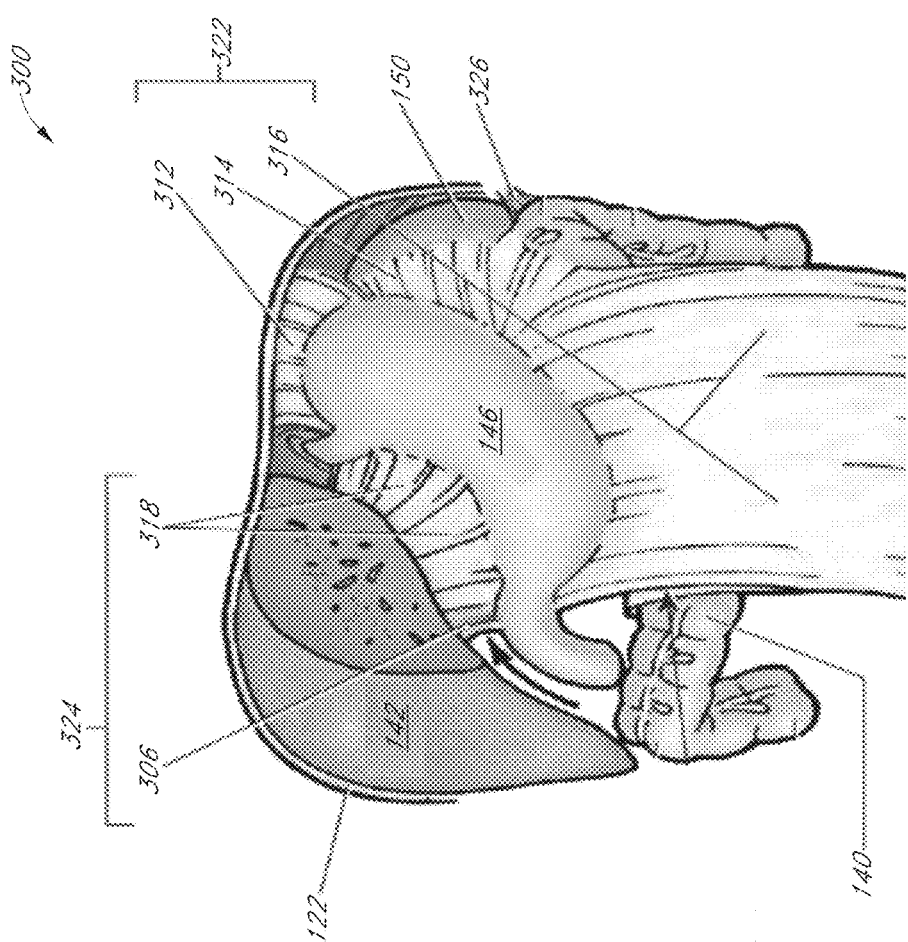
FIG. 3 illustrates a schematic of a ventral view of various anatomical structures and connective tissues in an abdominal region of a human.
Figure 4:
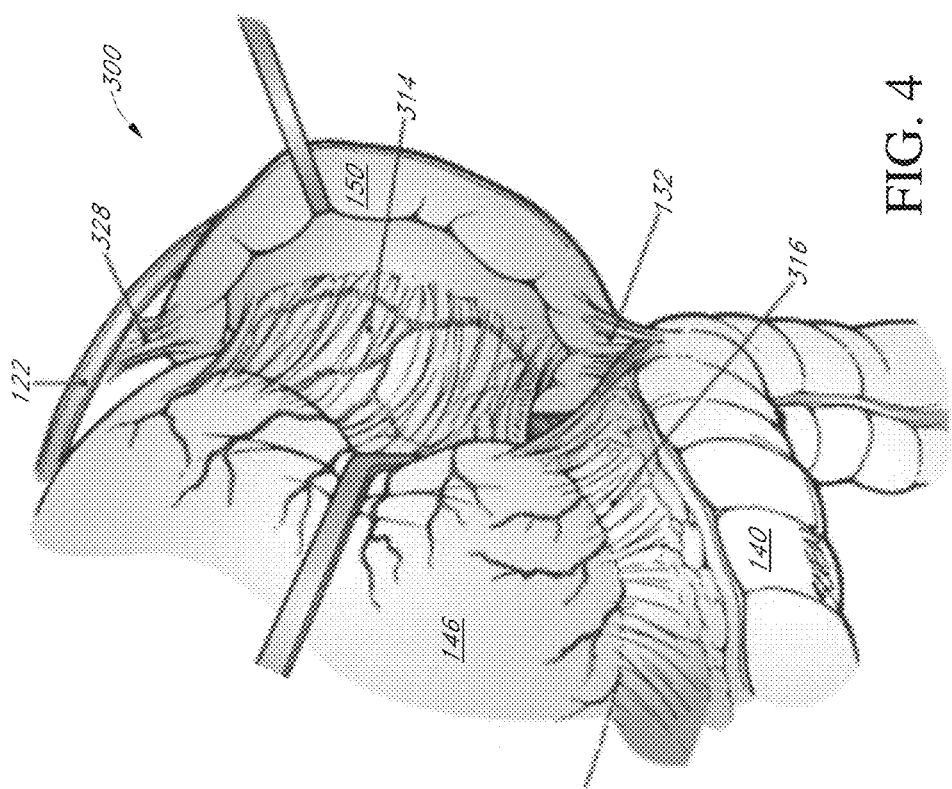
FIG. 4 illustrates a schematic of a lateral section of various anatomical structures and connective tissues in an abdominal region of a human.
Figure 5:
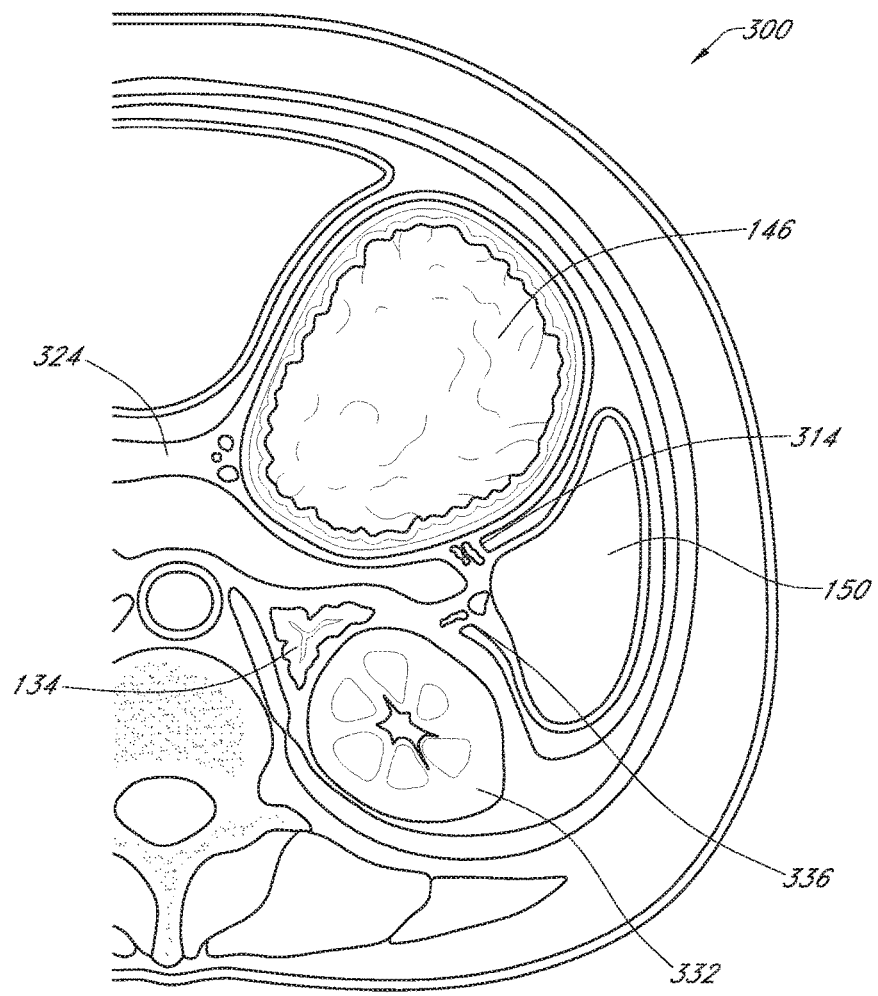
FIG. 5 illustrates a schematic of a transverse section of various anatomical structures and connective tissues in an abdominal region of a human.
Figure 6A:
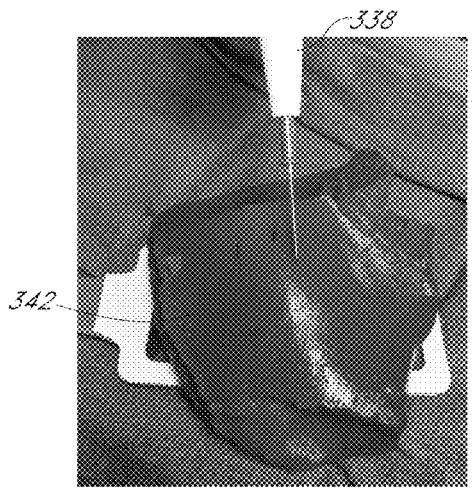
FIG. 6A shows a photograph of an electrosurgical tool and an anatomical structure before an application of energy by the electrosurgical tool to the anatomical structure.
Figure 6B:
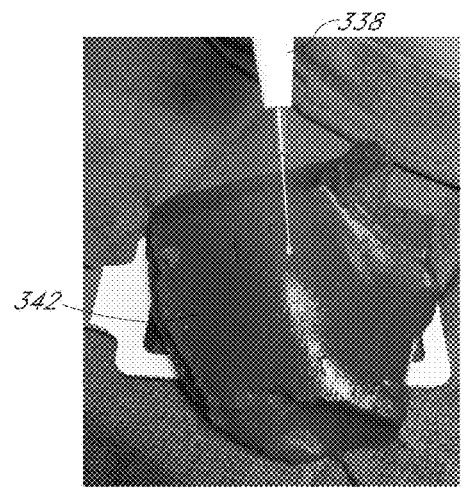
FIG. 6B shows a photograph of an electrosurgical tool and an anatomical structure at the start of an application of energy by the electrosurgical tool to the anatomical structure.
Figure 6C:
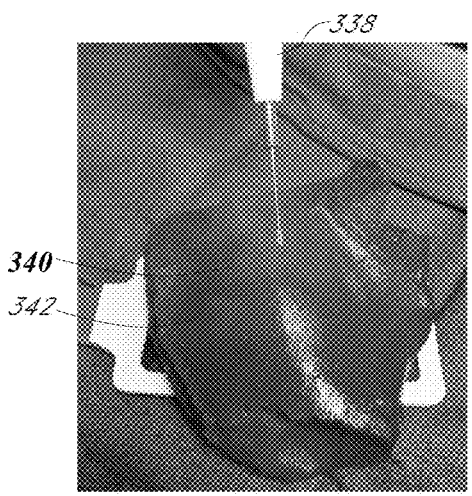
FIG. 6C shows a photograph of an electrosurgical tool and an anatomical structure during an application of energy by the electrosurgical tool to the anatomical structure.
Figure 6D:
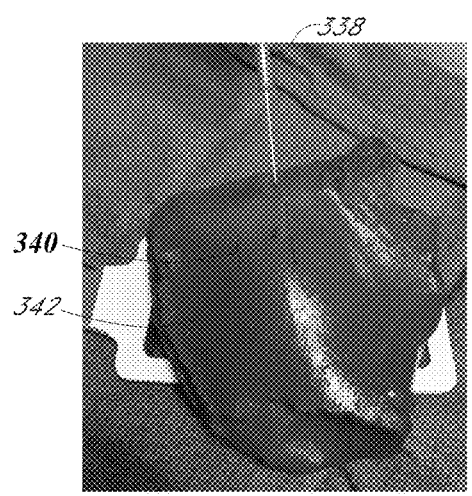
FIG. 6D shows a photograph of an electrosurgical tool and an anatomical structure after an application of energy by the electrosurgical tool to the anatomical structure.

In one embodiment, the surgical simulation system 100 may include features and/or structures that resemble aspects of the abdominal cavity of a human. However, it is to be appreciated that the surgical simulation system 100 may include additional form factors or simulate different regions of a human or animal body without departing from the original scope and intent of the present disclosure. FIGS. 3-5 show anatomy of the abdominal cavity 300 from various perspectives. As shown in FIG. 3, the stomach 146 is positioned anteriorly to the spleen 150, inferiorly to the spleen 150, and superiorly to the colon 140. In some embodiments, a first anatomical structure, for example the stomach 146, is coupled to a second anatomical structure via a connective tissue. For example, the stomach 146 is coupled to the diaphragm 122 via the gastrophrenic ligament 312, to the spleen 150 via the gastrosplenic ligament 314 (i.e., gastrolienal ligament), to the colon 140 via the gastrocolic ligament 316, and to the spleen 150 via the hepatogastric ligament 318 (i.e., gastrohepatic ligament); the gastrophrenic ligament 312, gastrosplenic ligament 314, and gastrocolic ligament 316 forming part of the greater omentum 322 and the hepatogastric ligament 318 forming part of the lesser omentum 324. In some embodiments, the first anatomical structure is a spleen 142. In one such embodiment, the spleen 142 is coupled to the small intestine via the hepatoduodenal ligament 306, forming part of the lesser omentum 324. In some embodiments, the first anatomical structure is a colon 140. In one such embodiment, the colon 140 is coupled to the diaphragm 122 via the phrenicocolic ligament 326. In some embodiments, the first anatomical structure is a spleen 150. In one such embodiment, as shown in FIG. 4, the spleen 150 is coupled to the diaphragm 122 via the phrenicosplenic ligament 328. In another embodiment, the spleen 150 is coupled to the colon 140 via the splenocolic ligament 132. In still another embodiment, as shown in FIG. 5, the spleen 150 is coupled to a kidney 332 and to the tail of the pancreas 134 via the splenorenal ligament 336 (i.e., lienorenal ligament or splenic-pancreatic ligament).

In some embodiments, a structure of the first anatomical structure and/or second structure is derived from a scan, for example a pre-operative scan. Non-limiting examples of scans include: computed tomography (CT) scan, a magnetic resonance imaging (MRI) scan, a conventional X-ray, an ultrasound imager, molecular imaging, or any type of medical imaging. In one embodiment, a structure of the first anatomical structure and/or the second anatomical structure is derived from a CT scan, for example from a de-identified patient or a known or identified patient.

In some embodiments, one or more of the first anatomical structure, the second anatomical structure, the connective tissue, and tubular structure is at least partially vaporized, sealed, and/or cut in response to an application of energy emitted by an electrosurgical tool. A natural response of a tissue to energy emitted by an electrosurgical tool is to dissociate or separate, at least partially vaporize, coagulate, cauterize, and/or seal. The structures described herein are configured to embody these features (e.g., cut, at least partially vaporize, coagulate and seal) to provide a near real tissue response during a simulated training session. As shown in FIGS. 6A-6D, application of energy with an electrosurgical tool 338 produces a cut 340 in the anatomical structure 342 and seals or cauterizes the cut in the anatomical structure 342.

Figure 7:
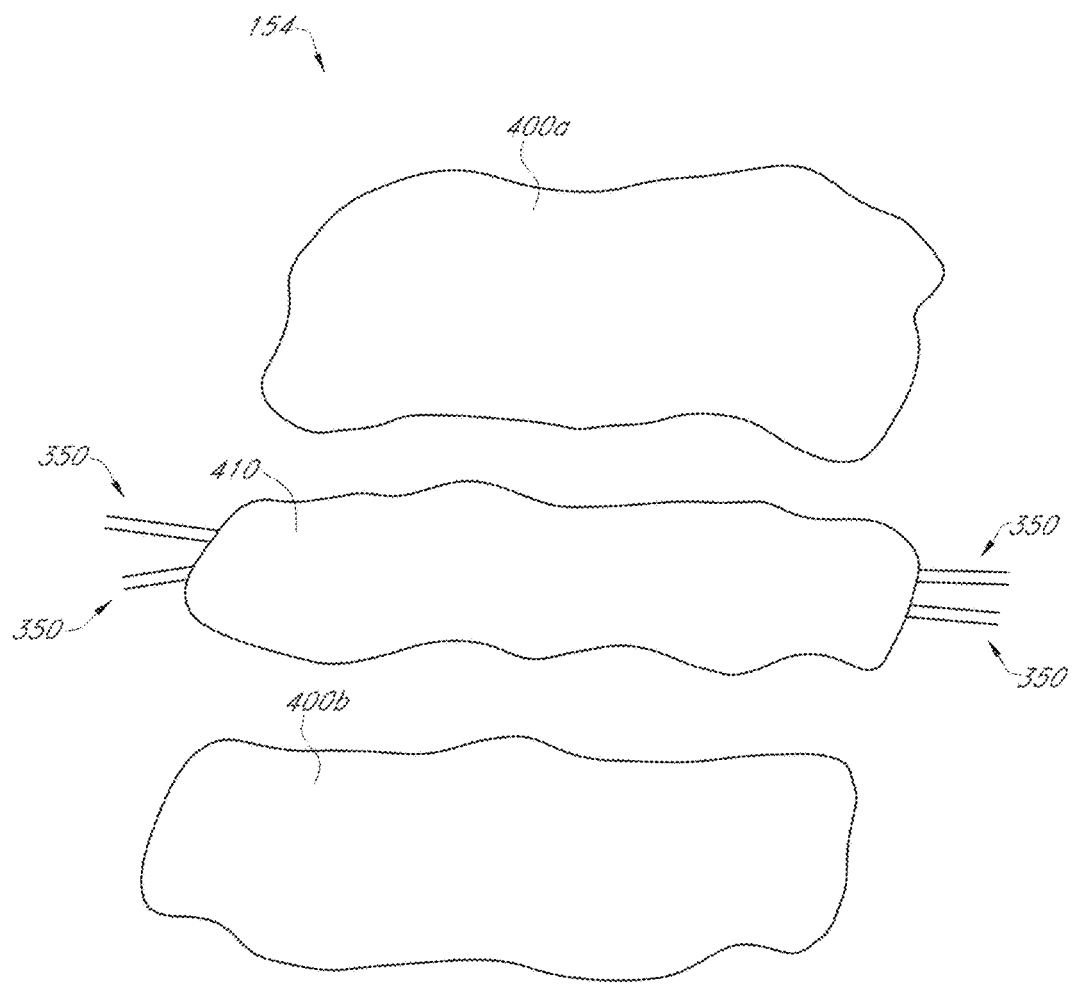
FIG. 7 illustrates one embodiment of three layers of connective tissues.

The connective tissue 154 functions to connect, support, bind, and/or separate other tissues and/or organs. Typically, connective tissue 154 includes an amorphous matrix, for example comprising collagen or other fibers, including cartilaginous, fatty, and elastic tissues. FIG. 7 shows a connective tissue 154 of a surgical simulation system 100 as described herein. The connective tissue 154 functions to at least partially conceal one or more tubular structures 350 so that the user can gain experience dissecting the tubular structures 350 without knowing the exact the location of the one or more tubular structures 350. For example, in some embodiments as shown in FIG. 7, a connective tissue 154 may include a top layer 400a (e.g., ligamentous layer), a bottom layer 400b (e.g., ligamentous layer), and a middle layer 410 (e.g., adipose-like tissue). In some embodiments, one or more tubular structures 350 are coupled to or partially or wholly embedded in the middle layer 410. Further, the top layer 400a and the bottom layer 400b function to partially or wholly encapsulate the middle layer 410.

In some embodiments, the tubular structure comprises a network of tubular structures. The network of tubular structures may comprise a plurality of interconnected tubular structures. In some embodiments, the network of tubular structures comprises one or more of a first portion at least partially embedded in a first anatomical structure or a first connective tissue, a second portion at least partially embedded in a second anatomical structure or a second connective tissue, and a third portion at least partially embedded in a third anatomical structure or a third connective tissue. In one such embodiment, the first portion, the second portion, and the third portion of the network of tubular structures are interconnected to further couple together the first anatomical structure, the connective tissue, and the second anatomical structure. In some embodiments, a network of tubular structures includes a fourth portion. In some such embodiments, the fourth portion of the network of tubular structures is coupled to one or more of the first portion, the second portion, and the third portion, such that the fourth portion extends from the housing and couples to a reservoir 116, for example as shown in FIG. 1.

In some embodiments, a complexity of a surgical simulation system 100 may be increased or decreased to alter a level of difficulty for a user using the surgical simulation system 100. For example, in some such embodiments, a tortuosity (i.e., number of curves, degree of twisting) of one or more of: the first portion, the second portion, the third portion, the nth portion may be altered to change a complexity of the surgical simulation system 100. Further, in some embodiments, a network of tubular structures may include n number of tubular structures, such that n can be increased or decreased to change a complexity of the surgical simulation system 100. Still further, in some embodiments, one or more of: a size, a shape, a stiffness, and a hardness of one or more of: the first anatomical structure, the second anatomical structure, the nth anatomical structure, the first connective tissue, the second connective tissue, the nth connective tissue, the first tubular structure, the second tubular structure, and the nth tubular structure is altered to change a complexity of the surgical simulation system 100.

Figure 8A:
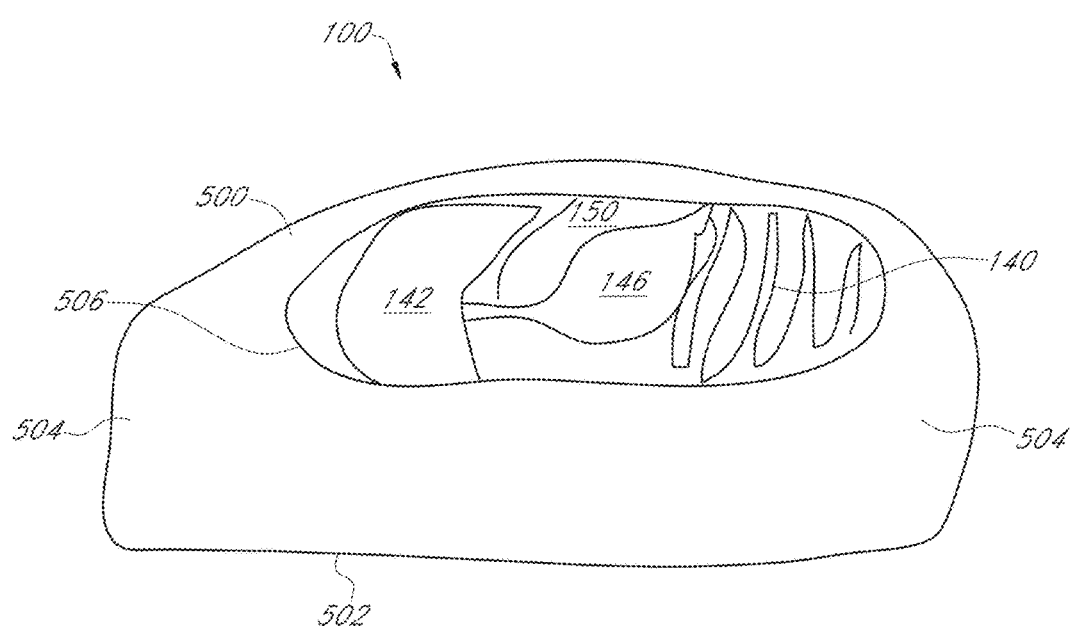
FIG. 8A illustrates a side view of one embodiment of a housing of a surgical simulation system.
Figure 8B:
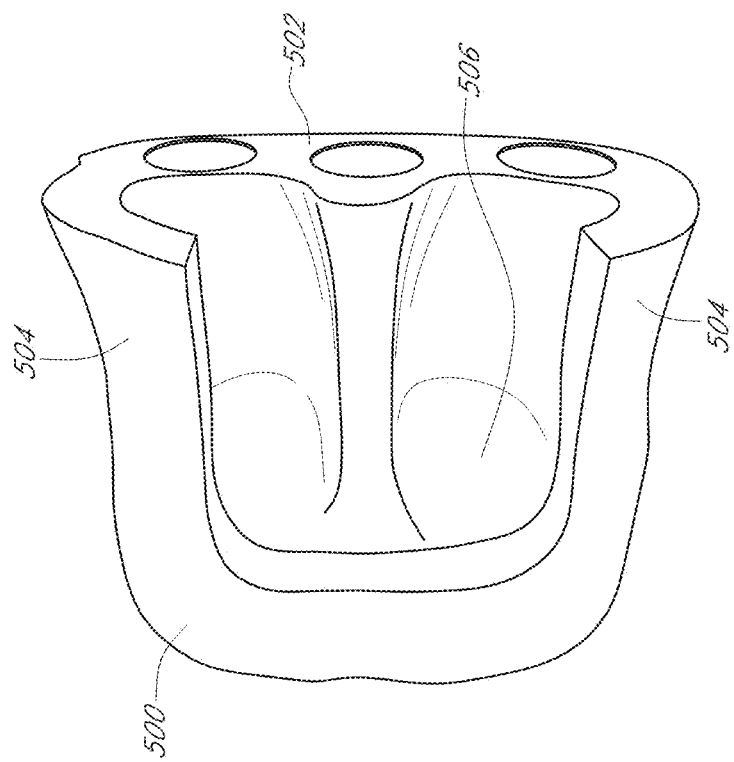
FIG. 8B illustrates a top perspective view of one embodiment of a housing of a surgical simulation system.

In some embodiments, as shown in FIGS. 8A-8B, a surgical simulation system 100 includes a housing 500. The housing 500 functions to house, support, or aggregate one or more anatomical structures, connective tissues, and/or tubular structures. The housing 500 may comprise a back panel 502 for contacting a surface, for example a table; a plurality of sidewalls 504 coupled to a perimeter of the back panel 502; and an aperture 506 defined by at least a subset of the plurality of sidewalls 504. The aperture 506 functions to allow a user to access one or more anatomical structures, connective tissues, and/or tubular structures in the surgical simulation system 100. In some embodiments, one or more of the plurality of sidewalls 504 are further configured to contact a surface, for example a table. The plurality of sidewalls 504 may be planar, curved, or beveled. In one embodiment, the plurality of sidewalls 504 of the housing 500 has an appearance similar to abdominal walls or the walls of an abdomen or skin, as shown in FIG. 8B. Alternatively, the plurality of sidewalls 504 may resemble a human or animal bodily structure that houses one or more anatomical structures, connective tissues, and/or tubular structures, for example an abdominal cavity, a chest cavity, a pelvic cavity, a leg, an arm, or a skull cavity. FIG. 8A illustrates one embodiment comprising the liver 142, the spleen 150, the stomach 146 and the colon 140. In some embodiments, the plurality of sidewalls include a plurality of internal sidewalls proximal the anatomical structures and a plurality of external sidewalls that resemble an exterior surface of a patient and/or contact a surface, such that a gap or cavity exists between the plurality of internal sidewalls and the plurality of external sidewalls. Portions or segments of simulated connective tissue and/or tubular structures may be threaded or fed through one or more apertures in the plurality of internal sidewalls and secured in the gap or cavity via a securing element (e.g., clamp) to limit movement of the connective tissue and/or tubular structures in the housing. In some embodiments, the securing element is obscured from exterior visualization by the plurality of external sidewalls. In other embodiments, there is no external sidewalls such that the securing element is visible on an exterior of the housing.

Figure 8C:
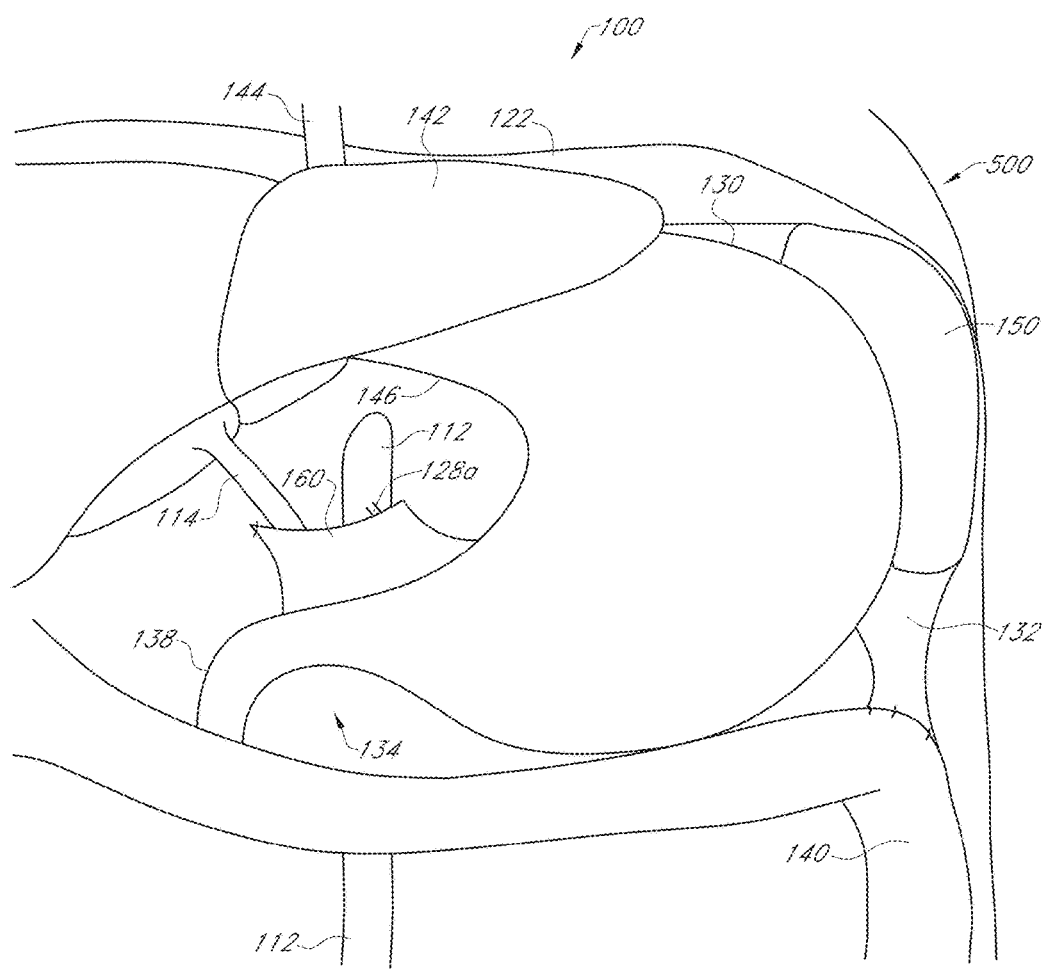
FIG. 8C illustrates a cross-sectional view of various anatomical structures in a housing before system use.

FIGS. 8C-11 show various embodiments of a surgical simulation system 100. FIG. 8C includes the stomach 146 while FIGS. 9-11 do not include the inferior portion of the stomach 146 to facilitate viewing structures positioned posteriorly to the stomach 146. Further, FIGS. 8-9 do not include a subset of the tubular structures while FIGS. 10-11 include various tubular structures or a network of tubular structures, for example tubular structures 126a, 126b, 128a, 128b.

Figure 9:
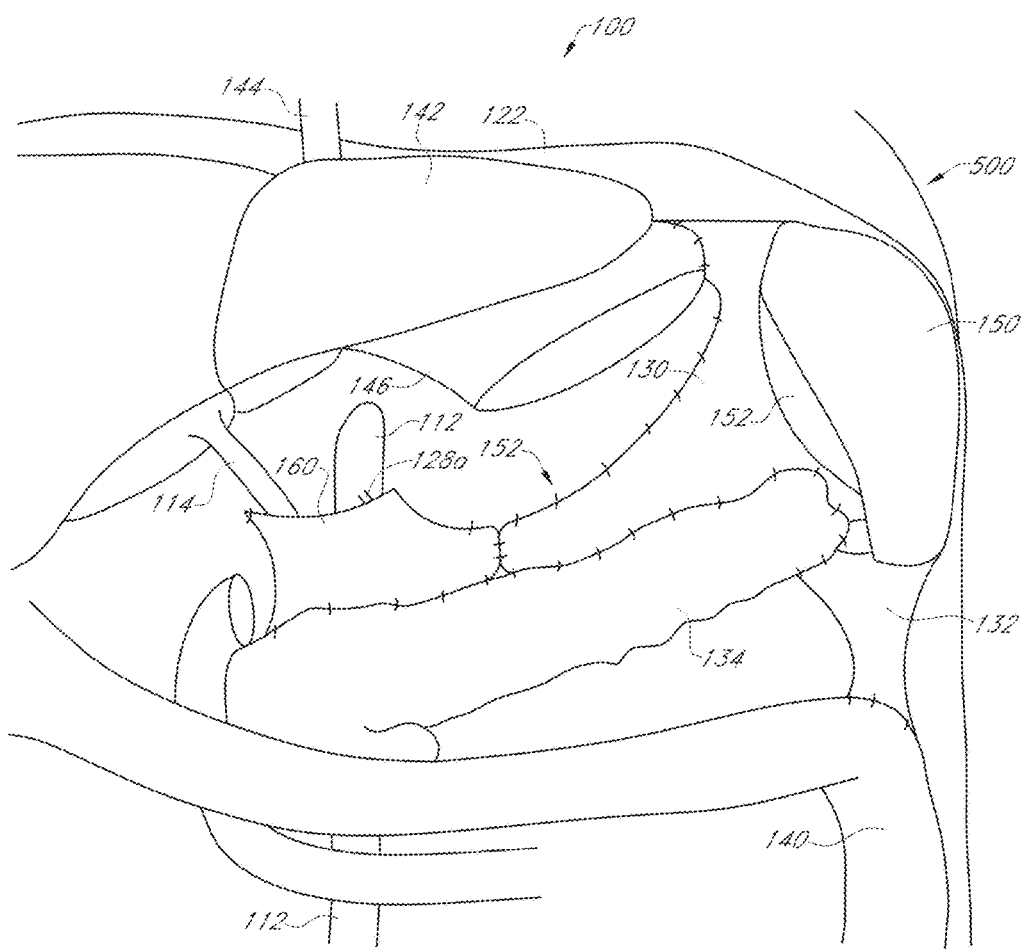
FIG. 9 illustrates a cross-sectional view similar to FIG. 8C but with one anatomical structure, an inferior portion of the stomach, removed.
Figure 10:
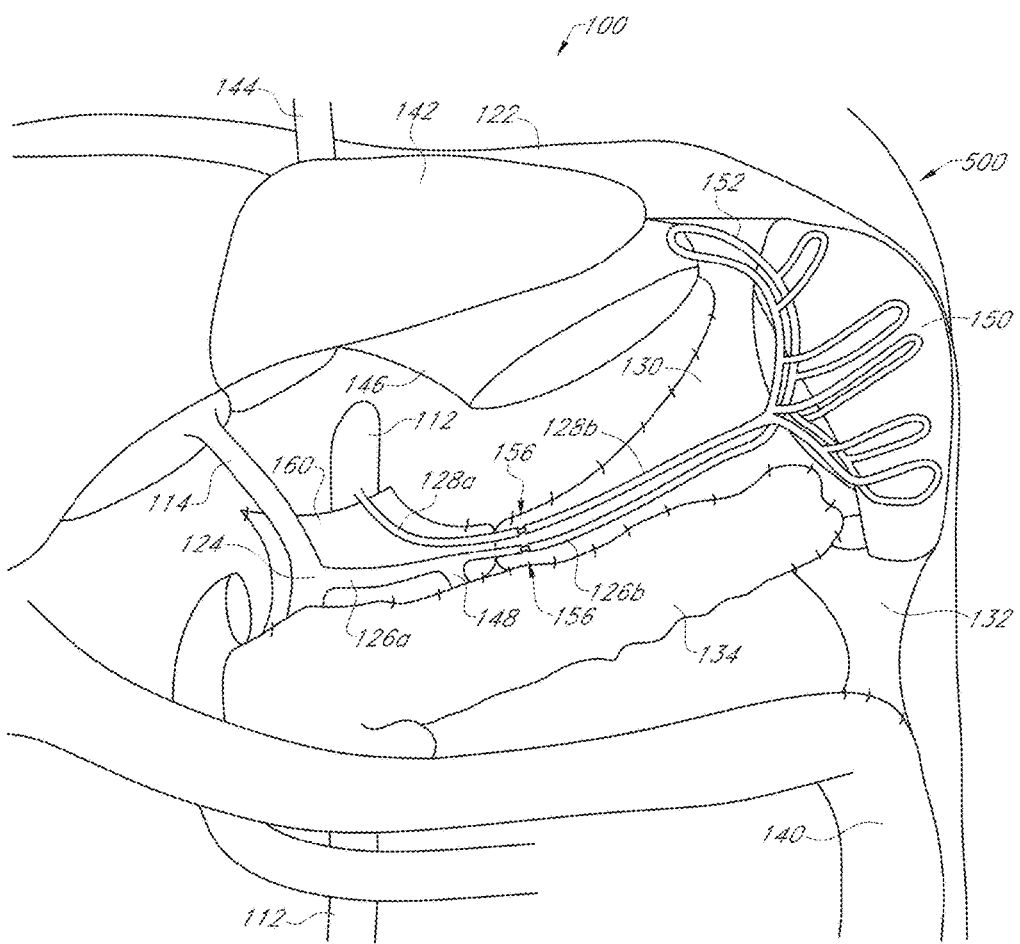
FIG. 10 illustrates a cross-sectional view of various anatomical structures and connective tissues coupled together and a network of tubular structures uncoupled from the connective tissue. In this view, an inferior portion of the stomach is removed.

In one embodiment, as shown in FIGS. 8C-11, a surgical simulation system 100 includes a plurality of anatomical structures, for example: a spleen 150, a stomach 146 (FIG. 8C), an esophagus 144, a duodenum 138, a liver 142, a gallbladder, small intestines, a colon/large intestines 140, a pancreas 134, and a diaphragm 122, all housed within the housing 500. In some embodiments, the spleen 150 includes the splenic hilum 151 (FIG. 9), which for example may be used as an identifying feature of the spleen during a simulation surgery or procedure. Alternatively or additionally, as shown in FIGS. 8C-11, a surgical simulation system 100 may include one or more tubular structures, for example an abdominal aorta 112, and as illustrated in FIG. 10, a superior mesenteric vein 124, a hepatic portal vein 114, an inferior mesenteric vein 148, a splenic artery 128, and/or a splenic vein 126. In some embodiments, each anatomical structure may be configured to stand alone inside the housing 500 or exterior to the housing 500. In some embodiments, one or more anatomical structures are coupled to another anatomical structure, for example via a connective tissue and/or tubular structure.

In some embodiments, as shown in FIG. 9, a surgical simulation system 100 includes a first anatomical structure 150 (e.g., spleen), a second anatomical structure 140 (e.g., colon), a third anatomical structure 134 (e.g., pancreas), a first connective tissue 130, 160 (e.g., first and second portions of splenopancreatic-splenogastric ligament, respectively), and a second connective tissue 132 (e.g., splenocolic ligament). In one non-limiting embodiment of the first connective tissue, a first end 160 may remain installed in the housing while a second end 130 may be replaced along with, for example, the first anatomical structure after each use. In some such embodiments, the first connective tissue 130 couples the first anatomical structure 150 to the third anatomical structure 134 and the second connective tissue 132 couples the first anatomical structure 150 to the second anatomical structure 140 and the third anatomical structure. Further, as shown in FIG. 9, if a fourth anatomical structure 146 (e.g., stomach) is included, the first connective tissue 130 would further couple the first anatomical structure 150 to the fourth anatomical structure 146. The coupling mechanism 152 will be described in further detail elsewhere herein.

Figure 11:
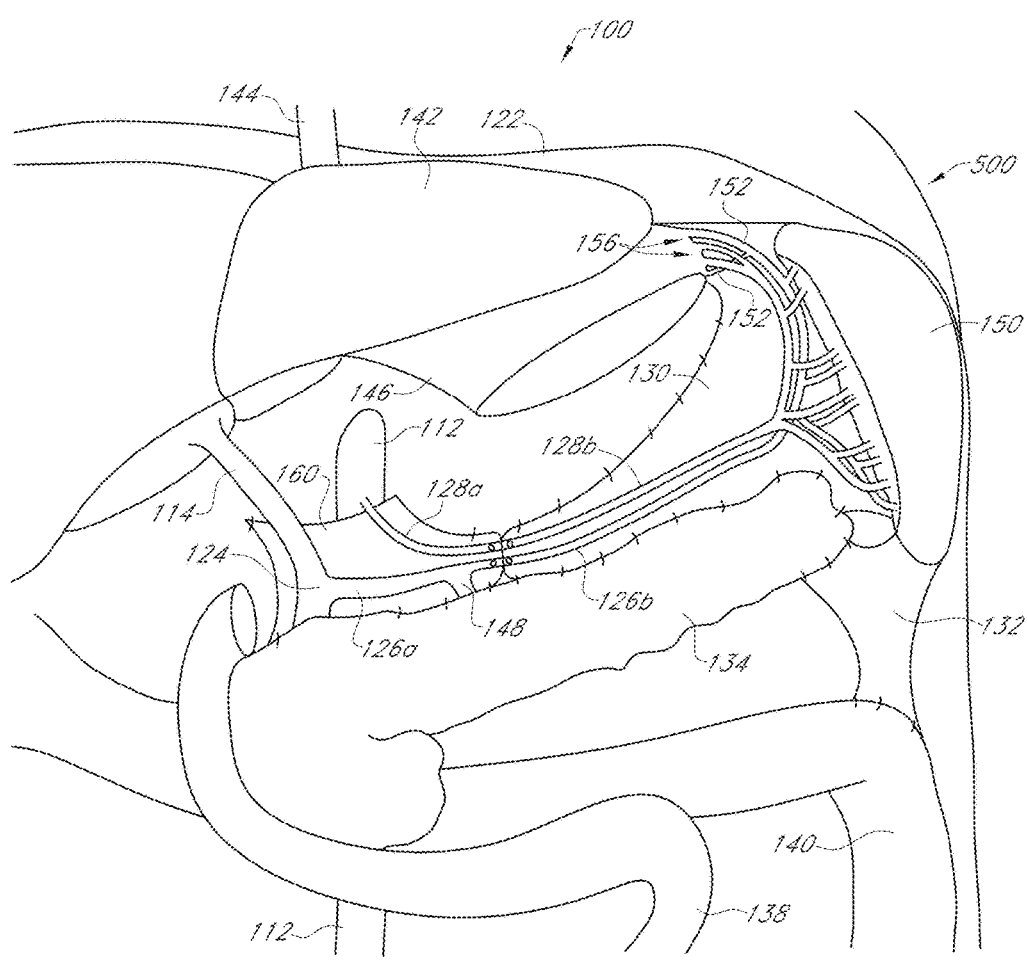
FIG. 11 illustrates a cross-sectional view of various anatomical structures and connective tissues coupled together and a network of tubular structures coupled to the connective tissue. In this view, an inferior portion of the stomach is removed.

In some embodiments, as shown in FIGS. 10-11, a first tubular structure 126 (e.g., splenic vein) and a second tubular structure 128 (e.g., splenic artery) are coupled to or at least partially embedded within the first connective tissue 130. In some such embodiments, the first tubular structure 126a (e.g., left splenic-gastric vein) and the second tubular structure 128a (e.g., left splenic gastric artery), couple to a third tubular structure 126b (e.g., right splenic-gastric vein) and a fourth tubular structure 128b (e.g., left splenic gastric artery), respectively, for example to form a network of tubular structures. Further, in some such embodiments, the third tubular structure 126b and the fourth tubular structure 128b couple to the first connective tissue 130 and to an anatomical structure 146, for example a superior portion of the stomach 146, as shown in FIG. 11. FIG. 10 shows the third tubular structure 126b and the fourth tubular structure 128b uncoupled from the first connective tissue 130 and FIG. 11 shows the third tubular structure 126b and the fourth tubular structure 128b coupled to the first connective tissue 130. The coupling mechanism shown in FIGS. 10-11 will be described in further detail elsewhere herein.

Figure 12A:
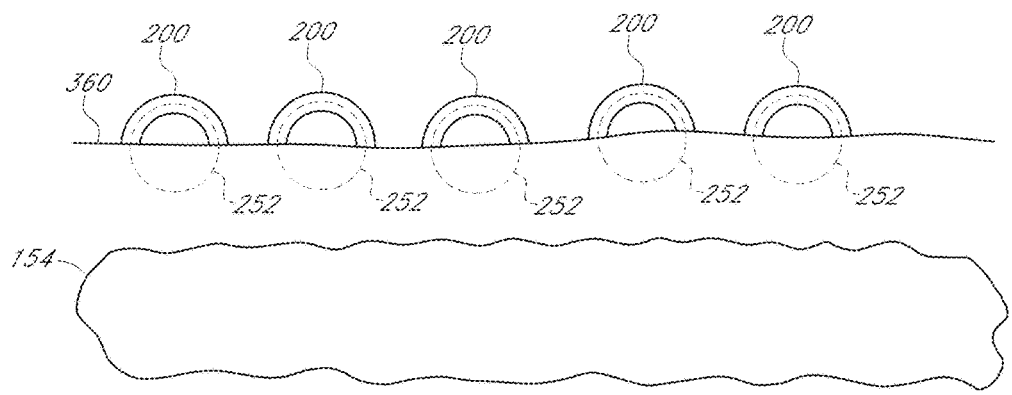
FIG. 12A illustrates one embodiment of an anatomical structure uncoupled from a connective tissue or a second anatomical structure.
Figure 12B:
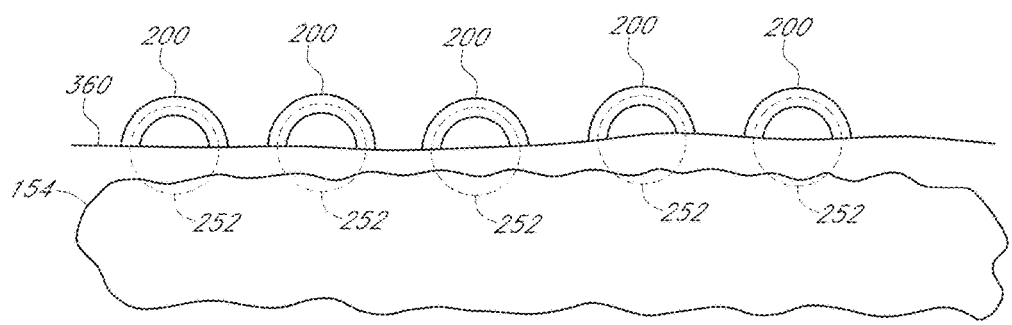
FIG. 12B illustrates one embodiment of an anatomical structure partially coupled to a connective tissue or a second anatomical structure.
Figure 12C:
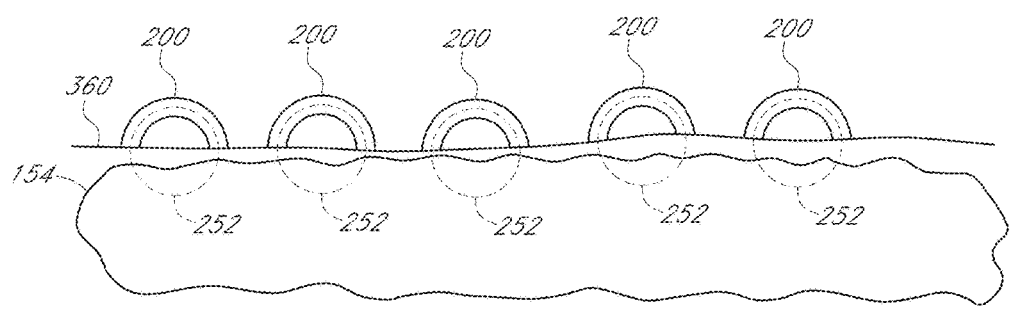
FIG. 12C illustrates one embodiment of an anatomical structure coupled to a connective tissue or a second anatomical structure.

FIGS. 12A-12C illustrate various stages of coupling a connective tissue to an anatomical structure using a coupling mechanism 152. The coupling mechanism 152 functions to secure the anatomical structure 360 to the connective tissue 154 while allowing the anatomical structure 360 to move and/or rotate in response to user activity. In some embodiments, the coupling mechanism 152 comprises fasteners, hooks, clips, buttons, clasps, or another type of coupler. In one embodiment, the coupling mechanism 152 comprises a plurality of hooks 152. In some embodiments, the coupling mechanism 152 is permanently housed on an anatomical structure 360; in other embodiments, the coupling mechanism 152 is removeably secured to the anatomical structure, for example to allow a user to adapt a number, type, or spacing of the coupling mechanism 152. The coupling mechanism 152 may pierce, puncture, or otherwise penetrate an eye or a portion of a connective tissue or second anatomical structure to couple the connective tissue or second anatomical structure to the first anatomical structure. In some embodiments, the coupling mechanism 152 is positioned along a perimeter of the connective tissue or anatomical structure; in other embodiments, the coupling mechanism 152 is positioned in a reinforced region, a region of increased thickness, or a non-perimeter portion of the connective tissue or anatomical structure. In some embodiments, piercing, puncturing, or penetrating occurs via application of direct force or application of a turning or spinning force to the coupling mechanism 152. In one non-limiting example, the first anatomical structure 146 (e.g., stomach) and a second anatomical structure 140 (e.g., colon) each include a coupling mechanism 152 for coupling a first connective tissue 130 (e.g., splenopancreatic-splenogastric ligament) to the first anatomical structure 146 and a second connective tissue 132 (e.g., splenocolic ligament) to the second anatomical structure 140. In some embodiments, as shown in FIGS. 12A-12C, to protect the anatomical structures 360 proximate to the operative site, a ring is housed on a distal end of a channel 200 embedded in and partially extending from the anatomical structure 360 to enable a hook slidably disposed in the ring to rotate or adjust its position in the ring to allow an anatomical structure 360 or connective tissue 154 coupled by the coupling mechanism 152 to move without being damaged. FIG. 12A shows the anatomical structure 360 uncoupled from the connective tissue 154. FIG. 12B shows the anatomical structure 360 partially coupled to the connective tissue 154. FIG. 12C shows the anatomical structure 360 fully coupled to the connective tissue 154.

Figure 13A:
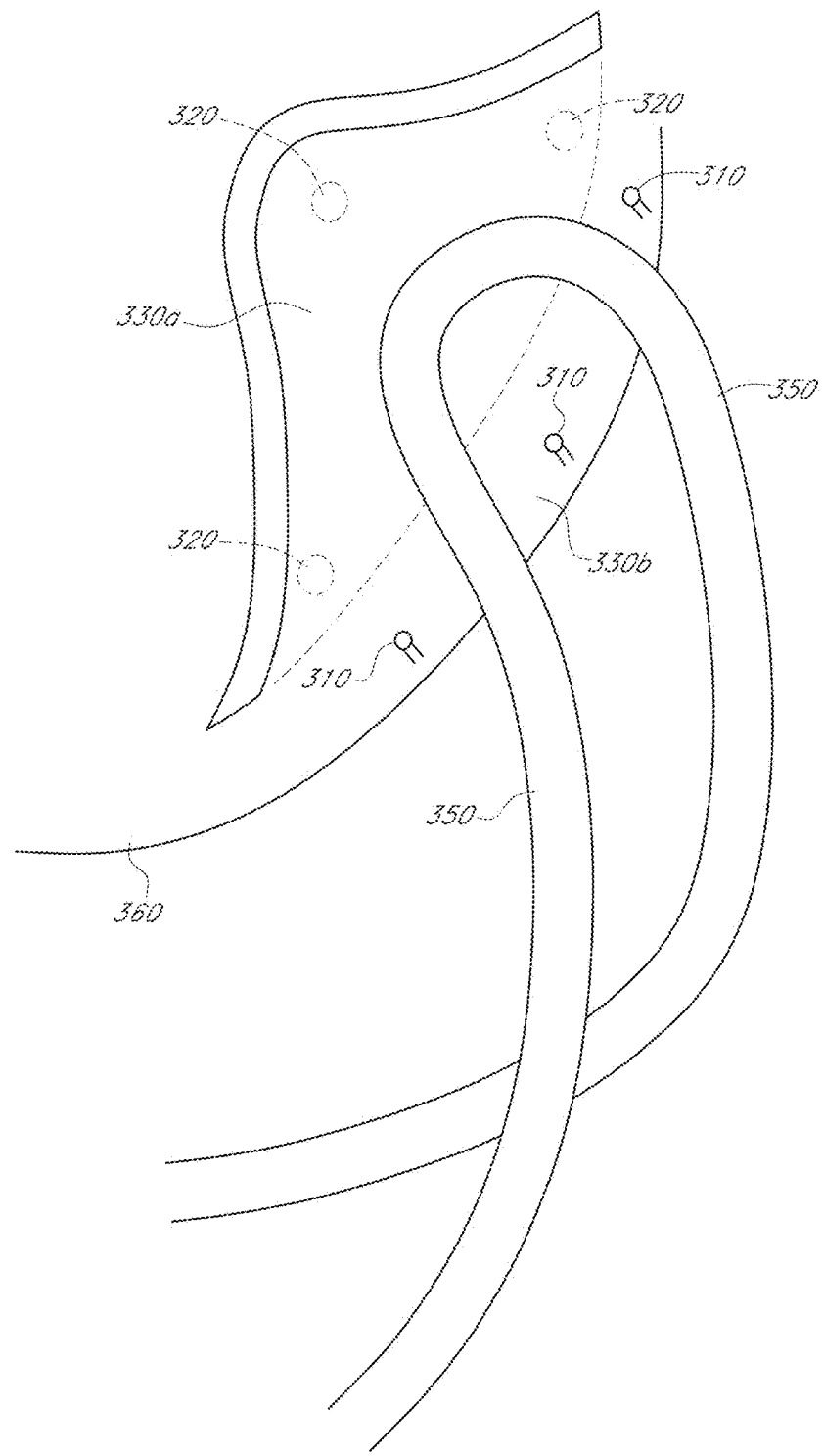
FIG. 13A illustrates one embodiment of a first tubular structure uncoupled from an anatomical structure or a connective tissue.
Figure 13B:
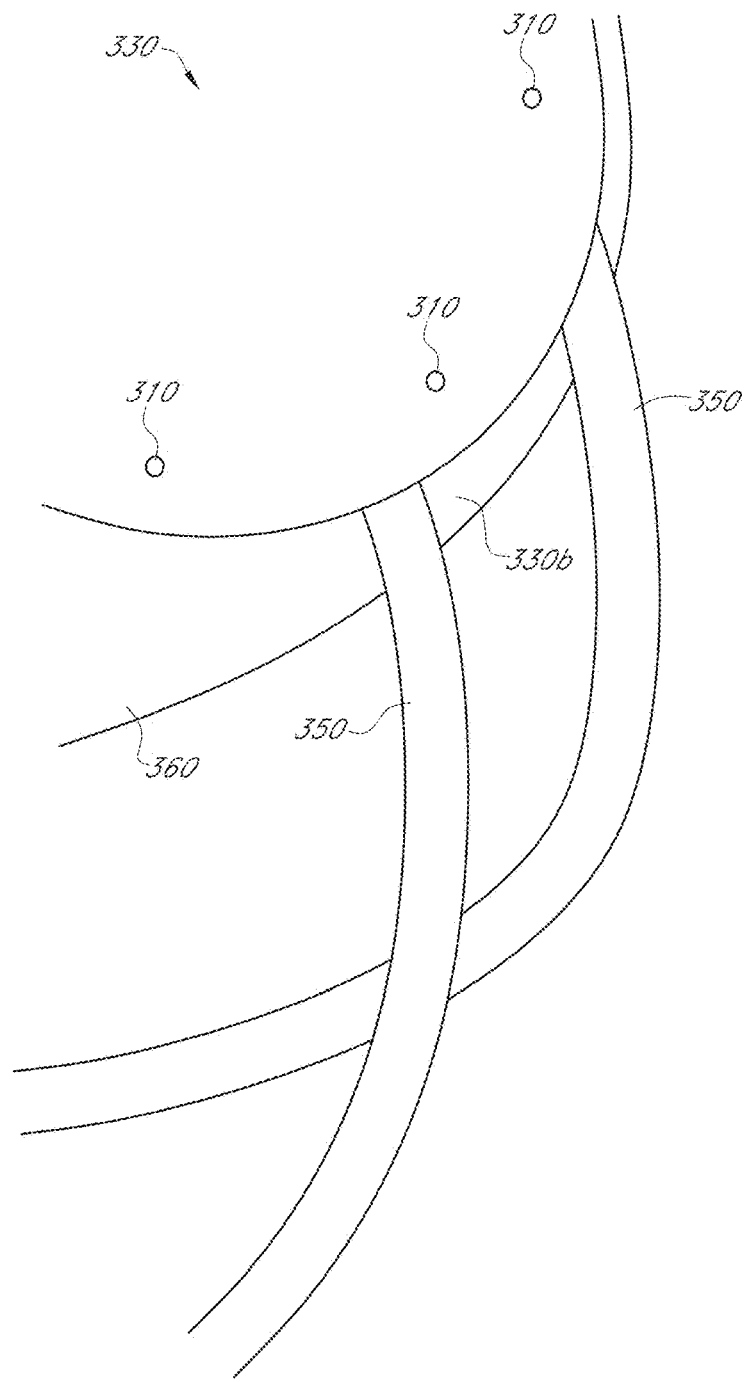
FIG. 13B illustrates one embodiment of a first tubular structure coupled to an anatomical structure or a connective tissue.

In some embodiments, a portion of a tubular structure may be coupled to an anatomical structure or connective tissue by securing the portion of the tubular structure with a fastener, button, clasp, clip, hook, or another type of coupler. In one non-limiting example, FIGS. 13A-13B show one embodiment of a coupling mechanism 320 for coupling a tubular structure 350 to an anatomical structure 360 or connective tissue 154. FIG. 13A shows a tubular structure 350 uncoupled from an anatomical structure 360 or connective tissue 154 and FIG. 13B shows a tubular structure 350 coupled to an anatomical structure 360 or connective tissue 154. In some embodiments, a looped portion of a tubular structure is secured between a top flap 330a and a bottom flap 330b of an anatomical structure 360 or a connective tissue 154. In some such embodiments, the top flap 330a includes an eyelet 320 and the bottom flap 330b includes a protrusion 310, for example a button, for securing the top flap 330a to the bottom flap 330b with the tubular structure 350 positioned and secured therebetween.

Figure 14A:
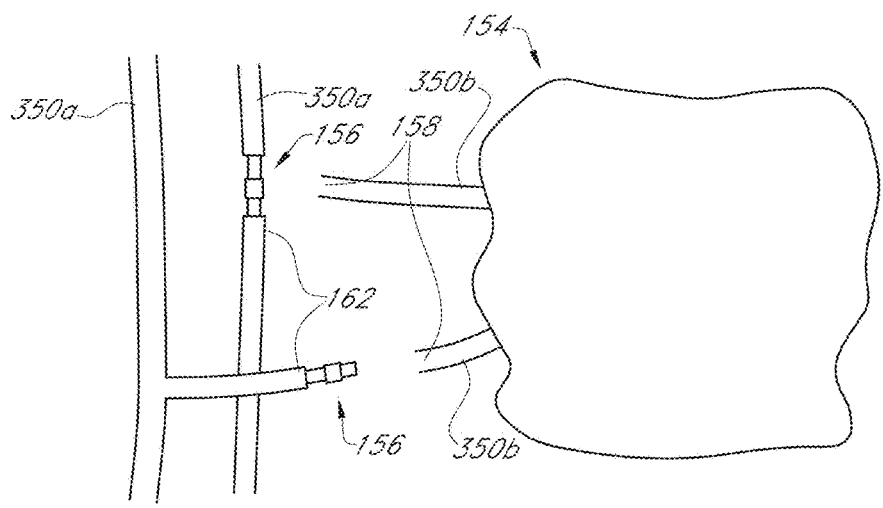
FIG. 14A illustrates one embodiment of a first tubular structure uncoupled from a second tubular structure.
Figure 14B:
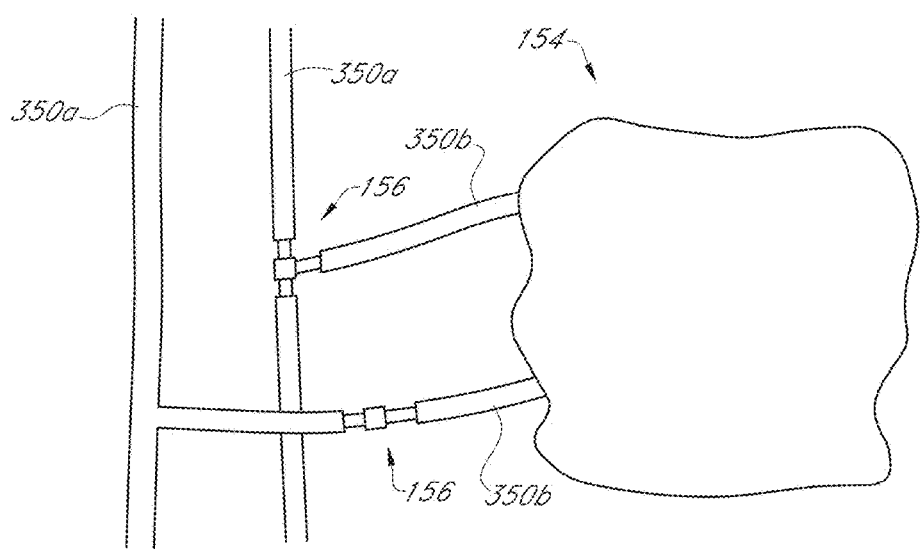
FIG. 14B illustrates one embodiment of a first tubular structure coupled to a second tubular structure.

In some embodiments, a first end 162 of a first tubular structure 350a may be coupled to a second end 158 of a second tubular structure 350b. In some such embodiments, the network of tubular structures is interconnected via a coupling mechanism 156, for example a series of complementary fasteners. For example, the tubular structure coupling mechanism 156 may include a screw-thread connection, a snap-fit connection, a male-female end connection, or another type of connection. In one non-limiting example, the tubular structure coupling mechanism 156 comprises a two-way or three-way mechanical connector in an uncoupled configuration as shown in FIG. 14A and a coupled configuration as shown in FIG. 14B.

Figure 15:
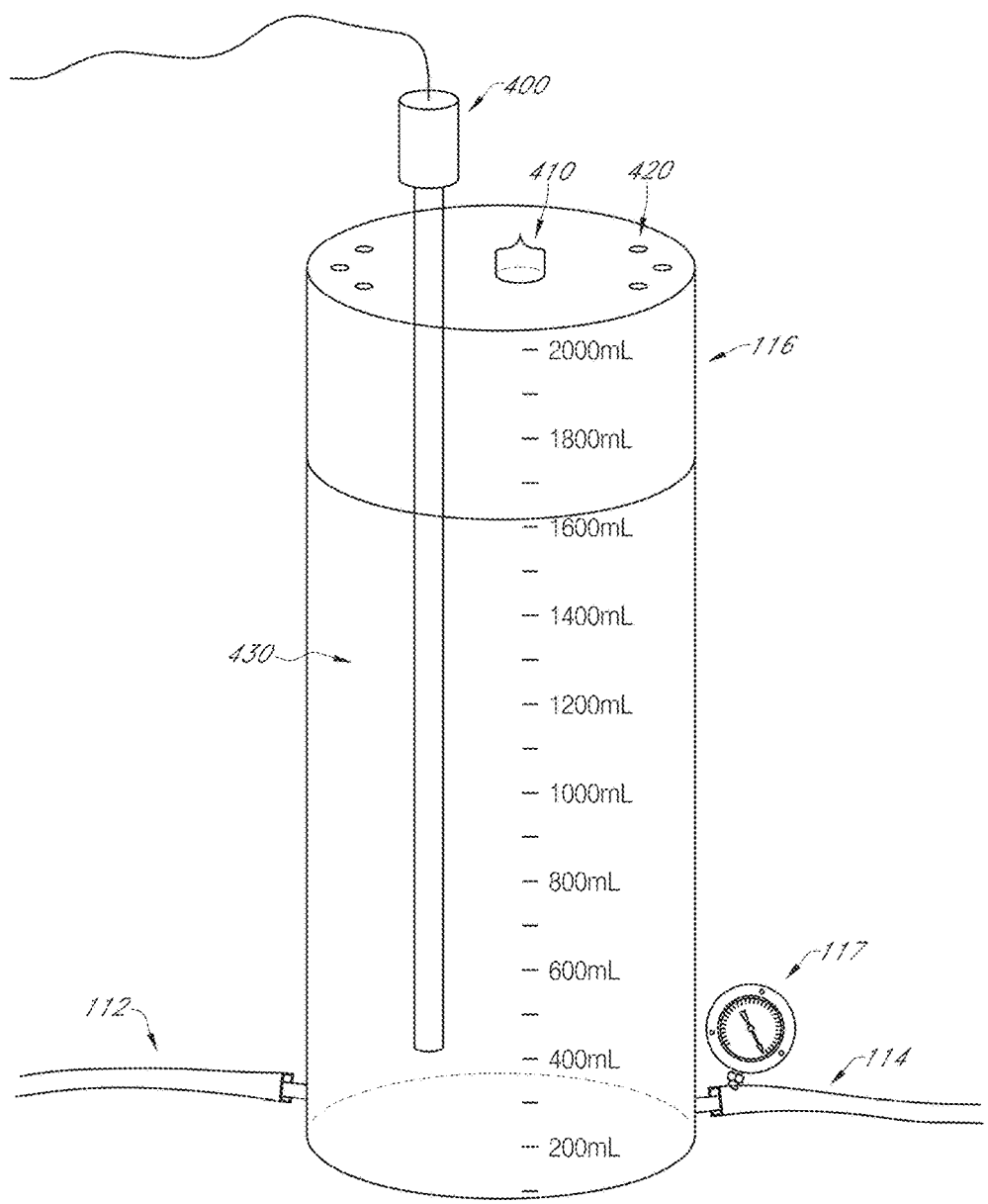
FIG. 15 illustrates one embodiment of a reservoir for storing a fluid for pumping through a surgical simulation system.

In some embodiments, as shown in FIG. 15, a surgical simulation system 100 includes a reservoir 116. The reservoir 116 functions to house and/or measure characteristics of a fluid 430 being pumped through the system in case of fluid loss during system use. In some embodiments, the reservoir 116 is a rigid structure or container; in other embodiments, the reservoir 116 is a flexible structure, for example a replaceable and/or resealable bag. The reservoir 116 is coupled to the system via one or more tubular structures, for example tubular structures 112, 114. In some embodiments, the reservoir 116 includes a liquid-measuring sensor 400 to measure one or more characteristics of a fluid in the reservoir 116. In some such embodiments, the liquid-measuring sensor 400 determines an amount of fluid loss by detecting a change in capacitance or resistance around the fluid 430 to determine a net change in the height of the fluid 430 around the sensor 400, as will be described in further detail elsewhere herein. In some embodiments, one or more characteristics of the fluid 430 is acquired or measured on-demand and/or continuously. In some embodiments, the reservoir 116 further includes a handle 410 to disconnect a top portion of the reservoir 116 from a bottom portion of the reservoir 116 to replenish a fluid in the reservoir. Further, in some embodiments, the reservoir 116 further includes one or more aeration apertures 420 to normalize the pressure inside of the reservoir 116 with the atmospheric pressure. The aeration apertures 420 may include a mechanical filter or filler to prevent microbes and/or debris from entering the reservoir 116. In some embodiments, as shown in FIG. 15, a surgical simulation system includes a pressure gauge 117, for example near or proximate to an outlet of the pump 118 or reservoir. The pressure gauge functions to measure a pressure of the fluid in the pump 118 and/or reservoir 116 to estimate fluid pressure in the system, for example to simulate blood pressure.

In some embodiments, as shown in FIG. 15, a surgical simulation system 100 includes a pressure gauge 117, for example near or proximate to an outlet of the pump 118 or reservoir 116. The pressure gauge 117 functions to measure a pressure of the fluid in the pump 118 and/or reservoir 116 to estimate fluid pressure in the system, for example to simulate blood pressure.

As shown in FIGS. 1-2, in some embodiments, a surgical simulation system includes a pump 118. The pump 118 functions to maintain a fluid in the surgical simulation system during operation. In some embodiments, the fluid is pumped in a pulsatile manner through the surgical simulation system. In some embodiments, the surgical simulation system is a closed loop system, such that there is substantially no discontinuity in fluid flow in the absence of user intervention (e.g., cutting, slicing, etc.). In some embodiments, the fluid 430 should not leave the system unless a user nicks or cuts a tubular structure either intentionally or unintentionally.

In some embodiments, the pump 118 creates a pressure gradient that drives the fluid to flow throughout one or more tubular structures in the system. In some embodiments, a size, network structure, intraluminal material resistance, and/or a distance from the pump 118 influences the flow rate. In some such embodiments, a smaller tubular structure, a network comprising increased branching, and/or a tubular structure distant from the pump 118 may experience a decrease in flow rate and less-pulsatile flow. For example, the splenic artery 128 branches off of the abdominal artery 112 resulting in a decrease in flow rate in the abdominal artery 128. For example, the superior mesenteric vein 124 and the inferior mesenteric vein 148 coalesce to form the hepatic portal vein 114 causing an increase in the flow rate in the hepatic portal vein 114. When one tubular structure branches into several tubular structures and then coalesce into a larger tubular structure, the pulsatile nature of the flow dissipates and the smaller tubular structures in the middle of the network act as a damper. The same effect occurs when an actual damper is used within the network. A damper functions to reduce the flow rate and a pressure gradient of a fluid entering it. For example, if the fluid entered in a pulsatile manner, the pulsatile nature of the fluid flow leaving the damper is minimal. Both of these designs mirror the effects of the capillaries within the body. At the capillaries, arterioles turn into venules after the red blood cells have given their oxygen supply to the surrounding tissues. In effect, capillaries are a damper of the first kind described; the arterioles continue to branch into smaller and smaller tubes and then eventually meet one another at the capillaries to become venules and eventually veins.

In some embodiments, a surgical simulation system 100 includes a fluid, for example synthetic blood. In some such embodiments, the fluid 430 is composed of a synthetic material, for example including any combination of one or more of the following: allura red, brilliant blue, and brilliant green dyes. In one embodiment of the system, the fluid flows from the reservoir 116, through the pump 118, and into a first tubular structure (e.g., abdominal aorta 112), into one or more additional tubular structures, and then returns back to the reservoir 116. In another embodiment of the system 100, the fluid flows from the reservoir 116 through a first tubular structure, into one or more additional tubular structure, to the pump 118, and then back to the reservoir 116.

Methods

Figure 16:
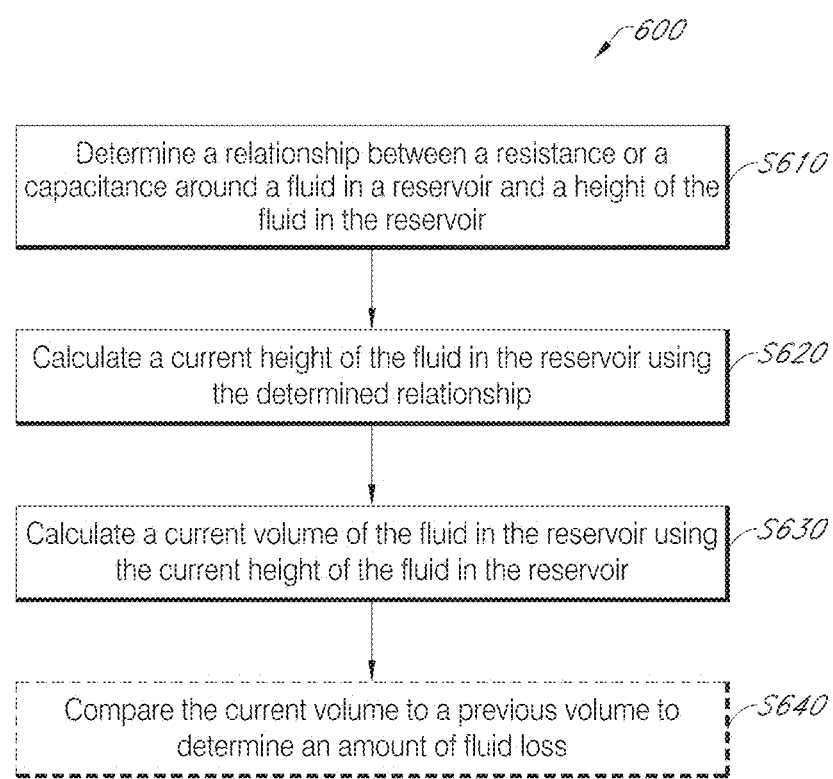
FIG. 16 illustrates one embodiment of a method of determining a fluid volume.

As shown in FIG. 16, a method 600 of determining a fluid volume includes block S610, which recites determining a relationship between a resistance or a capacitance around a fluid in a reservoir and a height of the fluid in the reservoir. Block S610 functions to calibrate the system to determine a relationship between a resistance or a capacitance around a fluid in a reservoir and a height of the fluid in the reservoir, which may vary from system to system or temporally. In some embodiments, a liquid sensor in the reservoir is calibrated to determine a relationship (e.g., linear, logarithmic, polynomial, exponential, etc.) between the resistance or capacitance and the height of the fluid inside of the reservoir.

As shown in FIG. 16, a method 600 of determining a fluid volume includes block S620, which recites calculating a current height of the fluid in the reservoir using the determined relationship. For example, if the relationship is linear, a net change in fluid height may be calculated using one of the following equations:

$$h = k_1 C + k_2 \text{ or } h = \frac{C - k_2}{k_1}$$

where h is a height of fluid inside of the reservoir; C is a capacitance; and $k_1$ and $k_2$ are the respective coefficients.

Note that if the liquid sensor uses resistance R instead of capacitance C, one of the following equations may be used:

$$h = k_1 R + k_2 \text{ or } h = \frac{R - k_2}{k_1}$$

where h is a height of fluid inside of the reservoir; R is a resistance; and $k_1$ and $k_2$ are the respective coefficients.

As shown in FIG. 16, a method 600 of determining a fluid volume includes block S630, which recites calculating a current volume of the fluid in the reservoir using the current height of the fluid in the reservoir. For example, once a height h of the fluid inside of the reservoir has been calculated, the following formula may be used to calculate a volume of the fluid inside of the reservoir:

$$V = \pi r^2 h$$

where V is the volume of the fluid inside of the reservoir; r is the radius of the container; and h is the calculated height of the fluid.

As shown in FIG. 16, a method 600 of determining a fluid volume optionally includes block S640, which recites comparing the current volume to a previous volume to determine an amount of fluid loss. In some embodiments, each volume measurement is compared to a previous volume measurement to determine an amount of fluid loss from the system. For example, if the first sample collected at $t_1$ reports a calculated volume inside the reservoir of 59 mL and the second sample at $t_2$ is 56 mL, the display will read that a net of 3 mL of fluid has been lost. This value will continue to update accordingly as long as the machine is in use.

In some embodiments, the liquid sensor stores measurements at a particular sampling frequency while the system is in use. In some such embodiments, the sampling frequency is regular, random, pre-programmed, or on-demand. In some embodiments, the sampling frequency ranges from 1 millisecond to 100 milliseconds, 100 milliseconds to 500 milliseconds, 500 milliseconds to 1 second, 1 second to five seconds, five seconds to ten seconds, or any subrange there between. In one such embodiment, the sampling frequency is every 1 millisecond, 2 milliseconds, 3 milliseconds, 4 milliseconds, or 5 milliseconds. In another embodiments, the sample frequency is every thirty seconds, one minute, five minutes, ten minutes, twenty minutes, twenty-five minutes, thirty minutes, thirty-five minutes, forty minutes, forty-five minutes, fifty minutes, fifty-five minutes, one hour, five hours, ten hours, or any range or subrange there between.

In some embodiments, a calculated value of net fluid volume loss as well as the net loss throughout the procedure is stored and presented to the user on a computing device when he/she is finished. The data may be stored in a user or administrator account, for example to determine improvement over time, to determine a grade or score for a procedure, or to compare a user's score to other scores in the system.

Figure 17:
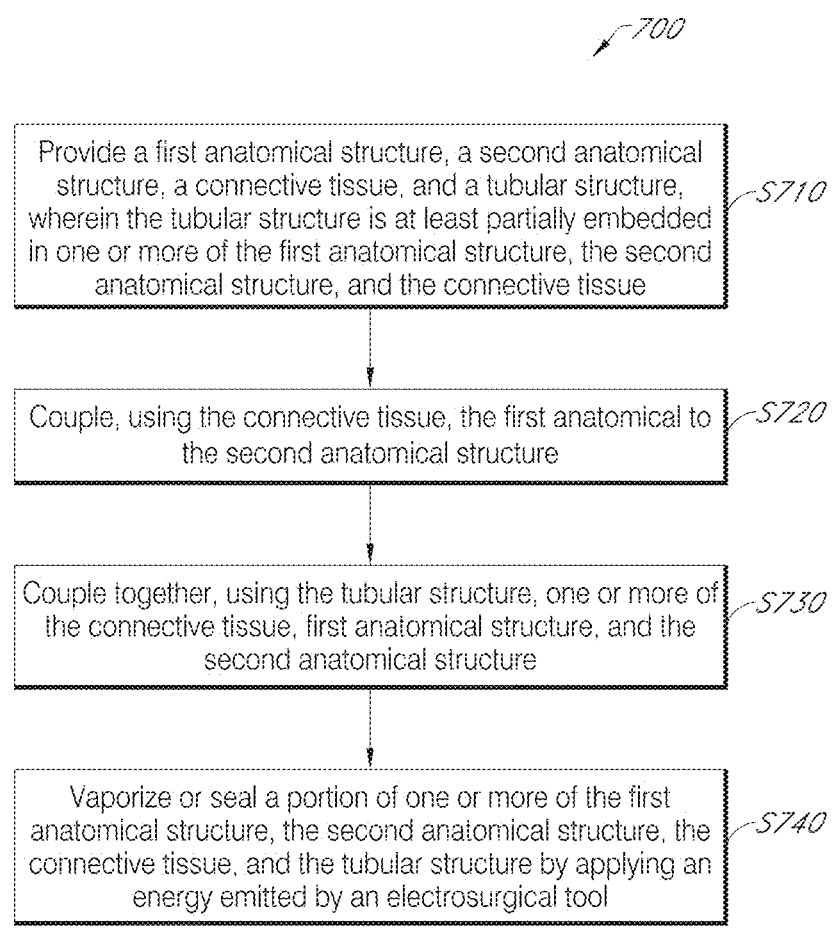
FIG. 17 illustrates one embodiment of a method of using a surgical simulation system.

As shown in FIG. 17, a method 700 of using a surgical simulation system for medical training of one embodiment includes providing a first anatomical structure, a second anatomical structure, a connective tissue, and a tubular structure, wherein the tubular structure is at least partially embedded in one or more of the first anatomical structure, the second anatomical structure, and the connective tissue S710; coupling, using the connective tissue, the first anatomical to the second anatomical structure S720; coupling together, using the tubular structure, one or more of the connective tissue, first anatomical structure, and the second anatomical structure S730; and vaporizing, sealing, and/or cutting a portion of one or more of the first anatomical structure, the second anatomical structure, the connective tissue, and the tubular structure by applying an energy emitted by an electrosurgical tool S740. Alternatively, in some embodiments, block S740 recites sealing or cutting a portion of one or more of the first anatomical structure, the second anatomical structure, the connective tissue, and the tubular structure using an endomechanical instrument, for example a stapler. The method functions to provide a near-real surgical experience for medical training, especially for training with electrosurgical tools. The method is used in the medical training field, but can additionally or alternatively be used for veterinary medicine or training, educational purposes, or any suitable application.

Compositions

Compositions to comprise the components of the surgical systems of the present invention such as the anatomical structure, the first anatomical structure, the second anatomical structure, the connective tissue and the tubular structure are selected so the synthetic structures respond to particular surgical instruments in a way that mimics human tissue response. To achieve this desired effect, anatomical structures are commonly made of thermoset polymers, although a mix of thermoset and thermoplastic polymers or thermoplastic polymer that retains the desired response to surgical instruments are also contemplated. Tubular networks are commonly made of a mixture of thermoset and thermoplastic polymers, although solely thermoset or solely thermoplastic polymers that retain the necessary rigidity for embedding and the desired response to surgical instruments are also contemplated.

In some embodiments, one or more of the anatomical structure, the first anatomical structure, the second anatomical structure, the connective tissue, and the tubular structure comprise one or more of: poly(ethylene glycol)-diacrylate gel, di(ethylene glycol)-dimethacrylate gel, ethylene glycol-diacrylate, poly(ethylene glycol)-diacrylate-ditetrathiol, poly(ethylene glycol)-methylmethacrylate, poly(ethylene glycol)-vinyl sulfone, poly(ethylene glycol)-amino-acrylate gel, poly(ethyelene glycol)-monamide, elastin-gelatin gel, elastin-collagen gel, collagen gel, gelatin gel, elastin gel, alginate gel, kappa-agar gel, locust bean gum (LBG)-agar gel, LBG-kappa gel, agarose gel, alginate-polyacrylamide gel, N-butylacrylamide gel, N-hexylacrylamide gel, N-octylacrylamide gel, N-dyhexylacrylamide gel, elastin-like polypeptides, gelatin-methacrylamide, alginate-polyacrylamide, polyvinyl chloride gel, cork, silk, chitosan, and chitosan-alginate gel, gelatin methacrylate, polylactic acid, poly-L-lactic acid, polyvinyl alcohol, fibrinogen, fibrinogen-collagen, fibrinogen-collagen-elastin, fibrinogen-thrombin gel, hyaluronic acid, polylactic-co-glycolic acid, polymethyl methacrylate, and polyurethane, as will be described in further detail elsewhere herein.

In some embodiments, the poly(ethylene glycol) diacrylate gel includes 0.05 mM to 1.5M poly(ethylene glycol)-diacrylate, 0.05 mM to 1.5M N-vinylpyrrolidone, 0.01 mM to 1.5M potassium persulfate, and 0.5 mM to 1.5M water. In one embodiment, the poly(ethylene glycol) diacrylate gel includes 1 mM to 1M poly(ethylene glycol)-diacrylate. In one embodiment, the poly(ethylene glycol) diacrylate gel includes 0.05 mM, 0.06 mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM, 0.9 mM, 1M, 1.1M, 1.2M, 1.3M, 1.4M, or 1.5M poly(ethylene glycol)-diacrylate. In one embodiment, the poly(ethylene glycol) diacrylate gel includes 1 mM to 1M N-vinylpyrrolidone. In one embodiment, the poly(ethylene glycol) diacrylate gel includes 0.05 mM, 0.06 mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM, 0.9 mM, 1M, 1.1M, 1.2M, 1.3M, 1.4M, or 1.5M N-vinylpyrrolidone. In one embodiment, the poly(ethylene glycol) diacrylate gel includes 0.5 mM to 1M potassium persulfate. In one embodiment, the poly(ethylene glycol) diacrylate gel includes 0.005 mM, 0.01 mM, 0.02 mM, 0.03 mM, 0.04 mM, 0.05 mM, 0.06 mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM, 0.9 mM, 1M, 1.1M, 1.2M, 1.3M, 1.4M, or 1.5M potassium persulfate. In one embodiment, the poly(ethylene glycol) diacrylate gel includes 1 mM to 1M water. In one embodiment, the poly(ethylene glycol) diacrylate gel includes 0.5 mM, 0.6 mM, 0.7 mM, 0.8 mM, 0.9 mM, 1M, 1.1M, 1.2M, 1.3M, 1.4M, or 1.5M water.

In some embodiments, the poly(ethylene glycol) diacrylate gel includes 1% weight/volume (w/v) to 50% w/v poly(ethylene glycol)-diacrylate, 1% w/v to 50% w/v N-vinylpyrrolidone, 1% w/v to 50% w/v potassium persulfate, and 1% w/v to 50% w/v water. In one embodiment, the poly(ethylene glycol) diacrylate gel includes 1-5%, 5-10%, 10-15%, 15-20%, 20-25%, 25-30%, 30-35%, 35-40%, 40-45%, 45-50% w/v, or any range or subrange there between of poly(ethylene glycol)-diacrylate. In one embodiment, the poly(ethylene glycol) diacrylate gel includes 1-5%, 5-10%, 10-15%, 15-20%, 20-25%, 25-30%, 30-35%, 35-40%, 40-45%, 45-50% w/v, or any range or subrange there between of N-vinylpyrrolidone. In one embodiment, the poly(ethylene glycol) diacrylate gel includes 1-5%, 5-10%, 10-15%, 15-20%, 20-25%, 25-30%, 30-35%, 35-40%, 40-45%, 45-50% w/v, or any range or subrange there between of potassium persulfate. In one embodiment, the poly(ethylene glycol) diacrylate gel includes 1-5%, 5-10%, 10-15%, 15-20%, 20-25%, 25-30%, 30-35%, 35-40%, 40-45%, 45-50% w/v, or any range or subrange there between of water.

In some embodiments, the diethylene glycol dimethacrylate gel comprises one or more of: diethylene glycol dimethacrylate, hydroethyl methacrylate (HEMA), N-vinylpyrrolidone, potassium persulfate, eosin Y, triethanolamine, and water.

In some embodiments, the poly(ethylene glycol)-amine-acrylate gel includes 0.5 mM to 1.5M poly(ethylene glycol)-aminoacrylate, 0.5 mM to 1.5M N-vinylpyrrolidone, 0.5 mM to 1.5M potassium persulfate, 0.5 mM to 1.5M water, 0.01 mM to 1.5M eosin Y, 150 mM to 750 mM triethanolamine, 1M to 10M cysteamine, and, optionally, Woodward's reagent K. In one embodiment, the poly(ethylene glycol)-amine-acrylate includes 1 mM to 1M poly(ethylene glycol)-aminoacrylate. In one embodiment, the poly(ethylene glycol)-amine-acrylate gel includes 0.5 mM, 0.6 mM, 0.7 mM, 0.8 mM, 0.9 mM, 1M, 1.1M, 1.2M, 1.3M, 1.4M, or 1.5M poly(ethylene glycol)-aminoacrylate. In one embodiment, the poly(ethylene glycol)-amine-acrylate includes 1 mM to 1M N-vinylpyrrolidone. In one embodiment, the poly(ethylene glycol)-amine-acrylate gel includes 0.5 mM, 0.6 mM, 0.7 mM, 0.8 mM, 0.9 mM, 1M, 1.1M, 1.2M, 1.3M, 1.4M, or 1.5M N-vinylpyrrolidone. In one embodiment, the poly(ethylene glycol)-amine-acrylate includes 1 mM to 1M potassium persulfate. In one embodiment, the poly(ethylene glycol)-amine-acrylate gel includes 0.5 mM, 0.6 mM, 0.7 mM, 0.8 mM, 0.9 mM, 1M, 1.1M, 1.2M, 1.3M, 1.4M, or 1.5M potassium persulfate. In one embodiment, the poly(ethylene glycol)-amine-acrylate includes 1 mM to 1M water. In one embodiment, the poly(ethylene glycol)-amine-acrylate gel includes 0.5 mM, 0.6 mM, 0.7 mM, 0.8 mM, 0.9 mM, 1M, 1.1M, 1.2M, 1.3M, 1.4M, or 1.5M water. In one embodiment, the poly(ethylene glycol)-amine-acrylate includes 0.05 mM to 1M eosin Y. In one embodiment, the poly(ethylene glycol)-amine-acrylate gel includes 0.01 mM, 0.02 mM, 0.03 mM, 0.04 mM, 0.05 mM, 0.06 mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM, 0.9 mM, 1M, 1.1M, 1.2M, 1.3M, 1.4M, or 1.5M eosin Y. In one embodiment, the poly(ethylene glycol)-amine-acrylate includes 225 mM to 500 mM triethanolamine. In one embodiment, the poly(ethylene glycol)-amine-acrylate gel includes 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, 300 mM, 310 mM, 320 mM, 330 mM, 340 mM, 350 mM, 360 mM, 370 mM, 380 mM, 390 mM, 400 mM, 500 mM, 510 mM, 520 mM, 530 mM, 540 mM, 550 mM, 560 mM, 570 mM, 580 mM, 590 mM, 600 mM, 610 mM, 620 mM, 630 mM, 640 mM, 650 mM, 660 mM, 670 mM, 680 mM, 690 mM, 700 mM, 710 mM, 720 mM, 730 mM, 740 mM, or 750 mM triethanolamine. In one embodiment, the poly(ethylene glycol)-amine-acrylate includes 1M, 1.5M, 2M, 2.5M, 3M, 3.5M, 4M, 4.5M, 5M, 5.5M, 6M, 6.5M, 7M, 7.5M, 8M, 8.5M, 9M, 9.5M, or 10M cysteamine. In one embodiment, the poly(ethylene glycol)-amine-acrylate includes 5.2M cysteamine.

In some embodiments, the poly(ethylene glycol)-amine-acrylate gel includes 0% w/v to 50% w/v poly(ethylene glycol)-aminoacrylate, 0% w/v to 50% w/v N-vinylpyrrolidone, 0% w/v to 50% w/v potassium persulfate, 0% w/v to 50% w/v water, 0% w/v to 50% w/v eosin Y, 0% w/v to 50% w/v triethanolamine, 0% w/v to 50% w/v cysteamine, and, optionally, Woodward's reagent K. In one embodiment, the poly(ethylene glycol)-amine-acrylate gel includes 0-5%, 5-10%, 10-15%, 15-20%, 20-25%, 25-30%, 30-35%, 35-40%, 40-45%, 45-50% w/v, or any range or subrange there between of poly(ethylene glycol)-aminoacrylate. In one embodiment, the poly(ethylene glycol)-amine-acrylate gel includes 0-5%, 5-10%, 10-15%, 15-20%, 20-25%, 25-30%, 30-35%, 35-40%, 40-45%, 45-50% w/v, or any range or subrange there between of N-vinylpyrrolidone. In one embodiment, the poly(ethylene glycol)-amine-acrylate gel includes 0-5%, 5-10%, 10-15%, 15-20%, 20-25%, 25-30%, 30-35%, 35-40%, 40-45%, 45-50% w/v, or any range or subrange there between of potassium persulfate. In one embodiment, the poly(ethylene glycol)-amine-acrylate gel includes 0-5%, 5-10%, 10-15%, 15-20%, 20-25%, 25-30%, 30-35%, 35-40%, 40-45%, 45-50% w/v, or any range or subrange there between of water. In one embodiment, the poly(ethylene glycol)-amine-acrylate gel includes 0-5%, 5-10%, 10-15%, 15-20%, 20-25%, 25-30%, 30-35%, 35-40%, 40-45%, 45-50% w/v, or any range or subrange there between of eosin Y. In one embodiment, the poly(ethylene glycol)-amine-acrylate gel includes 0-5%, 5-10%, 10-15%, 15-20%, 20-25%, 25-30%, 30-35%, 35-40%, 40-45%, 45-50% w/v, or any range or subrange there between of triethanolamine. In one embodiment, the poly(ethylene glycol)-amine-acrylate includes 0-5%, 5-10%, 10-15%, 15-20%, 20-25%, 25-30%, 30-35%, 35-40%, 40-45%, 45-50% w/v, or any range or subrange there between of cysteamine.

In some embodiments, the elastin-gelatin gel includes: 0.005 g/mL to 1 g/mL elastin, 0.005 g/mL to 1 g/mL gelatin, 0.0005% v/v to 0.1% v/v glutaraldehyde, and water. In one embodiment, the elastin-gelatin gel includes: 0.01 g/mL elastin. In one embodiment, the elastin-gelatin gel includes: 0.005 g/mL, 0.006 g/mL, 0.007 g/mL, 0.008 g/mL, 0.009 g/mL, 0.01 g/mL, 0.02 g/mL, 0.03 g/mL, 0.04 g/mL, 0.05 g/mL, 0.06 g/mL, 0.07 g/mL, 0.08 g/mL, 0.09 g/mL, 0.1 g/mL, 0.2 g/mL, 0.3 g/mL, 0.4 g/m, 0.5 g/mL, 0.6 g/mL, 0.7 g/mL, 0.8 g/mL, 0.9 g/mL, or 1 g/mL elastin. In one embodiment, the elastin-gelatin gel includes: 0.01 g/mL gelatin. In one embodiment, the elastin-gelatin gel includes: 0.005 g/mL, 0.006 g/mL, 0.007 g/mL, 0.008 g/mL, 0.009 g/mL, 0.01 g/mL, 0.02 g/mL, 0.03 g/mL, 0.04 g/mL, 0.05 g/mL, 0.06 g/mL, 0.07 g/mL, 0.08 g/mL, 0.09 g/mL, 0.1 g/mL, 0.2 g/mL, 0.3 g/mL, 0.4 g/m, 0.5 g/mL, 0.6 g/mL, 0.7 g/mL, 0.8 g/mL, 0.9 g/mL, or 1 g/mL gelatin. In one embodiment, the elastin-gelatin gel includes: 0.001% v/v glutaraldehyde. In one embodiment, the elastin-gelatin gel includes: 0.0005% v/v, 0.0006% v/v, 0.0007% v/v, 0.0008% v/v, 0.0009% v/v, 0.001% v/v, 0.002% v/v, 0.003% v/v, 0.004% v/v, 0.005% v/v, 0.006% v/v, 0.007% v/v, 0.008% v/v, 0.009% v/v, 0.01% v/v, 0.02% v/v, 0.03% v/v, 0.04% v/v, 0.05% v/v, 0.06% v/v, 0.07% v/v, 0.08% v/v, 0.09% v/v, or 0.1% v/v glutaraldehyde.

In some embodiments, the elastin-gelatin gel includes: 0% w/v to 50% w/v elastin, 0% w/v to 50% w/v gelatin, 0% w/v to 50% w/v glutaraldehyde, and water. In one embodiment, the elastin-gelatin gel includes: 0-5%, 5-10%, 10-15%, 15-20%, 20-25%, 25-30%, 30-35%, 35-40%, 40-45%, 45-50% w/v, or any range or subrange there between of elastin. In one embodiment, the elastin-gelatin gel includes: 0-5%, 5-10%, 10-15%, 15-20%, 20-25%, 25-30%, 30-35%, 35-40%, 40-45%, 45-50% w/v, or any range or subrange there between of gelatin. In one embodiment, the elastin-gelatin gel includes: 0-5%, 5-10%, 10-15%, 15-20%, 20-25%, 25-30%, 30-35%, 35-40%, 40-45%, 45-50% w/v, or any range or subrange there between of glutaraldehyde.

In some embodiments, an elastin-collagen gel comprises one or more of elastin, collagen, glutaraldehyde, and water. In some embodiments, a collagen gel includes one or more of collagen, phosphate buffered saline, hydrochloric acid, and sodium hydroxide.

In some embodiments, a gelatin gel comprises: 0% w/v to 50% w/v gelatin. In some embodiments, a gelatin gel comprises: 0.005% w/v to 15% w/v or 0.01% w/v to 10% w/v gelatin. In one embodiment, a gelatin gel comprises 0% w/v, 0.005% w/v, 0.01% w/v, 0.015% w/v, 0.02% w/v, 0.025% w/v, 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of gelatin.

In some embodiments, an elastin gel comprises: 0% w/v to 50% w/v elastin. In some embodiments, an elastin gel comprises 0.005% w/v to 15% w/v or 0.01% w/v to 10% w/v elastin. In one embodiment, a elastin gel comprises 0% w/v. 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of elastin.

In some embodiments, an alginate gel comprises: 0.5 mM to 15M sodium alginate and 0.5 mM to 15M calcium chloride. In one embodiment, an alginate gel includes 1 mM to 10M sodium alginate. In one embodiment, an alginate gel comprises: 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM, 11 mM, 12 mM, 13 mM, 14 mM, or 15 mM sodium alginate. In one embodiment, an alginate gel includes 1 mM to 10M calcium chloride. In one embodiment, an alginate gel comprises: 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM, 11 mM, 12 mM, 13 mM, 14 mM, or 15 mM calcium chloride.

In some embodiments, an alginate gel comprises: 0% w/v to 50% w/v sodium alginate and 0% w/v to 50% w/v calcium chloride. In some embodiments, an alginate gel comprises 0.005% w/v to 15% w/v or 0.01% w/v to 10% w/v sodium alginate. In one embodiment, an alginate gel comprises 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of sodium alginate. In one embodiment, an alginate gel comprises 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of calcium chloride.

In some embodiments, a kappa-agar gel comprises: 0.05% w/v to 1.5% w/v kappa carrageenan, 0.05% w/v to 1.5% w/v agar, and water. In one embodiment, a kappa agar gel includes: 0.05% w/v, 0.06% w/v, 0.07% w/v, 0.08% w/v, 0.09% w/v, 1.0% w/v, 1.1% w/v, 1.2% w/v, 1.3% w/v, 1.4% w/v, or 1.5% w/v kappa carrageenan. In one embodiment, a kappa agar gel comprises 0.1% w/v kappa carrageenan. In one embodiment, a kappa agar gel includes: 0.05% w/v, 0.06% w/v, 0.07% w/v, 0.08% w/v, 0.09% w/v, 1.0% w/v, 1.1% w/v, 1.2% w/v, 1.3% w/v, 1.4% w/v, or 1.5% w/v agar. In one embodiment, a kappa agar gel comprises 0.1% w/v agar.

In some embodiments, a kappa-agar gel comprises: 0% w/v to 50% w/v kappa carrageenan, 0% w/v to 50% w/v agar, and water. In one embodiment, a kappa agar gel includes: 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of kappa carrageenan. In one embodiment, a kappa agar gel includes: 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of agar.

In some embodiments, a LBG-agar gel comprises: 0% w/v to 50% w/v locus bean gum, 0% w/v to 50% w/v agar, and water. In one embodiment, a LBG-agar gel includes: 0.05% w/v, 0.06% w/v, 0.07% w/v, 0.08% w/v, 0.09% w/v, 1.0% w/v, 1.1% w/v, 1.2% w/v, 1.3% w/v, 1.4% w/v, or 1.5% w/v locus bean gum. In one embodiment, a LBG agar gel comprises 0.1% w/v locus bean gum. In one embodiment, a LBG-agar gel includes: 0.05% w/v, 0.06% w/v, 0.07% w/v, 0.08% w/v, 0.09% w/v, 1.0% w/v, 1.1% w/v, 1.2% w/v, 1.3% w/v, 1.4% w/v, or 1.5% w/v agar. In one embodiment, a LBG agar gel includes 0.1% w/v agar.

In some embodiments, a LBG-agar gel comprises: 0.05% w/v to 1.5% w/v locus bean gum, 0.05% w/v to 1.5% w/v agar, and water. In one embodiment, a LBG-agar gel includes: 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of locus bean gum. In one embodiment, a LBG-agar gel includes: 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of agar.

In some embodiments, a LBG-kappa gel includes: 0.05% w/v to 1.5% w/v locus bean gum, 0.05% w/v to 1.5% w/v kappa carrageenan, and water. In one embodiment, a LBG-kappa gel includes: 0.05% w/v, 0.06% w/v, 0.07% w/v, 0.08% w/v, 0.09% w/v, 1.0% w/v, 1.1% w/v, 1.2% w/v, 1.3% w/v, 1.4% w/v, or 1.5% w/v locus bean gum. In one embodiment, a LBG-kappa gel comprises 0.1% w/v locus bean gum. In one embodiment, a LBG-kappa gel includes: 0.05% w/v, 0.06% w/v, 0.07% w/v, 0.08% w/v, 0.09% w/v, 1.0% w/v, 1.1% w/v, 1.2% w/v, 1.3% w/v, 1.4% w/v, or 1.5% w/v kappa carrageenan. In one embodiment, a LBG-kappa gel comprises 0.1% w/v kappa carrageenan.

In some embodiments, a LBG-kappa gel includes: 0% w/v to 50% w/v locus bean gum, 0% w/v to 50% w/v kappa carrageenan, and water. In one embodiment, a LBG-kappa gel includes: 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of locus bean gum. In one embodiment, a LBG-kappa gel includes: 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of kappa carrageenan.

In some embodiments, an agarose gel includes 0.005% w/v to 30% w/v agarose and 25% to 99% w/v TAE buffer. In one embodiment, an agarose gel includes 0.01% w/v to 20% w/v agarose. In one embodiment, an agarose gel includes 0.005% w/v, 0.01% w/v, 0.1% w/v, 1.0% w/v, 2.5% w/v, 5% w/v, 10% w/v, 15% w/v, or 20% w/v agarose. In one embodiment, an agarose gel includes 50% w/v to 99% w/v TAE buffer. In one embodiment, an agarose gel includes 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 99% w/v TAE buffer.

In some embodiments, an agarose gel includes 0% w/v to 50% w/v agarose and 0% w/v to 50% w/v TAE buffer. In one embodiment, an agarose gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of agarose. In one embodiment, an agarose gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of TAE buffer.

In some embodiments, an alginate-polyacrylamide gel includes sodium alginate and acrylamide.

In some embodiments, an N-butylacrylamide gel includes 0% w/v to 99% w/v acrylamide, 0% w/v to 100% w/v N-butylacrylamide, 0% w/v to 99% w/v polyacrylamide, 0 mM to 5M or 0%-50% w/v ammonium persulfate, 0 mM to 5M or 0%-50% w/v N'-methylenebis(acrylamide), 0 mM to 5M or 0%-50% w/v N,N,N',N'-tetramethylethylenediamine, and 0 mM to 5M or 0%-50% w/v sodium dodecyl sulfate (SDS). In one embodiment, an N-butylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 99% w/v acrylamide. In one embodiment, an N-butylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 100% w/v N-butylacrylamide. In one embodiment, an N-butylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 99% w/v polyacrylamide. In one embodiment, an N-butylacrylamide gel includes 0 mM, 1 mM, 2 mM, 3 mM, 4 mM, or 5 mM ammonium persulfate. In another embodiment, an N-butylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of ammonium persulfate. In one embodiment, an N-butylacrylamide gel includes 0 mM, 1 mM, 2 mM, 3 mM, 4 mM, or 5 mM N'-methylenebis (acrylamide). In another embodiment, an N-butylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of N'-methylenebis(acrylamide). In one embodiment, an N-butylacrylamide gel includes 0 mM, 1 mM, 2 mM, 3 mM, 4 mM, or 5 mM N,N,N',N'-tetramethylethylenediamine. In another embodiment, an N-butylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of N,N,N',N'-tetramethylethylenediamine. In one embodiment, an N-butylacrylamide gel includes 0 mM, 1 mM, 2 mM, 3 mM, 4 mM, or 5 mM SDS. In another embodiment, an N-butylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, 50-55% w/v, 55-60% w/v, 60-65% w/v, 65-70% w/v, 70-75% w/v, 75-80% w/v, 80-85% w/v, 85-90% w/v, 90-95% w/v, or 95-99% w/v or any range or subrange there between of SDS.

In some embodiments, an N-hexylacrylamide gel includes 0% w/v to 99% w/v acrylamide, 0% w/v to 100% w/v N-hexylacrylamide, 0% w/v to 99% w/v polyacrylamide, 0 mM to 5M or 0%-50% w/v ammonium persulfate, 0 mM to 5M or 0%-50% w/v N'-methylenebis(acrylamide), 0 mM to 5M or 0%-50% w/v N,N,N',N'-tetramethylethylenediamine, and 0 mM to 5M sodium dodecyl sulfate (SDS). In one embodiment, an N-hexylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 99% w/v acrylamide. In one embodiment, an N-hexylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 100% w/v N-hexylacrylamide. In one embodiment, an N-hexylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 99% w/v polyacrylamide. In one embodiment, an N-hexylacrylamide gel includes 0 mM, 1 mM, 2 mM, 3 mM, 4 mM, or 5 mM ammonium persulfate. In another embodiments, an N-hexylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of ammonium persulfate. In one embodiment, an N-hexylacrylamide gel includes 0 mM, 1 mM, 2 mM, 3 mM, 4 mM, or 5 mM N'-methylenebis (acrylamide). In another embodiment, an N-hexylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of N'-methylenebis(acrylamide). In one embodiment, an N-hexylacrylamide gel includes 0 mM, 1 mM, 2 mM, 3 mM, 4 mM, or 5 mM N,N,N',N'-tetramethylethylenediamine. In another embodiment, an N-hexylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of N,N,N',N'-tetramethylethylenediamine. In one embodiment, an N-hexylacrylamide gel includes 0 mM, 1 mM, 2 mM, 3 mM, 4 mM, or 5 mM SDS. In one embodiment, an N-hexylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, 50-55% w/v, 55-60% w/v, 60-65% w/v, 65-70% w/v, 70-75% w/v, 75-80% w/v, 80-85% w/v, 85-90% w/v, 90-95% w/v, or 95-99% w/v or any range or subrange there between of SDS.

In some embodiments, an N-octylacrylamide gel includes 0% w/v to 99% w/v acrylamide, 0% w/v to 100% w/v N-octylacrylamide, 0% w/v to 99% w/v polyacrylamide, 0 mM to 5M or 0%-50% w/v ammonium persulfate, 0 mM to 5M or 0%-50% w/v N'-methylenebis(acrylamide), 0 mM to 5M or 0%-50% w/v N,N,N',N'-tetramethylethylenediamine, and 0 mM to 5M sodium dodecyl sulfate (SDS). In one embodiment, an N-octylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 99% w/v acrylamide. In one embodiment, an N-octylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 100% w/v N-octylacrylamide. In one embodiment, an N-octylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 99% w/v polyacrylamide. In one embodiment, an N-octylacrylamide gel includes 0 mM, 1 mM, 2 mM, 3 mM, 4 mM, or 5 mM ammonium persulfate. In another embodiments, an N-octylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of ammonium persulfate. In one embodiment, an N-octylacrylamide gel includes 0 mM, 1 mM, 2 mM, 3 mM, 4 mM, or 5 mM N'-methylenebis(acrylamide). In another embodiment, an N-octylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of N'-methylenebis(acrylamide). In one embodiment, an N-octylacrylamide gel includes 0 mM, 1 mM, 2 mM, 3 mM, 4 mM, or 5 mM N,N,N',N'-tetramethylethylenediamine. In another embodiment, an N-octylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of N,N,N',N'-tetramethylethylenediamine. In one embodiment, an N-octylacrylamide gel includes 0 mM, 1 mM, 2 mM, 3 mM, 4 mM, or 5 mM SDS. In one embodiment, an N-octylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, 50-55% w/v, 55-60% w/v, 60-65% w/v, 65-70% w/v, 70-75% w/v, 75-80% w/v, 80-85% w/v, 85-90% w/v, 90-95% w/v, or 95-99% w/v or any range or subrange there between of SDS.

In some embodiments, an N-dihyxylacrylamide gel includes 0% w/v to 99% w/v acrylamide, 0% w/v to 100% w/v N-dihyxylacrylamide, 0% w/v to 99% w/v polyacrylamide, 0 mM to 5M or 0%-50% ammonium persulfate, 0 mM to 5M or 0%-50% N'-methylenebis(acrylamide), 0 mM to 5M or 0%-50% N,N,N',N'-tetramethylethylenediamine, and 0 mM to 5M sodium dodecyl sulfate (SDS). In one embodiment, an N-dihyxylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 99% w/v acrylamide. In one embodiment, an N-dihyxylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 100% w/v N-dihyxylacrylamide. In one embodiment, an N-dihyxylacrylamide gel includes 0% w/v, 5% w/v, 10% w/v, 15% w/v, 20% w/v, 25% w/v, 30% w/v, 35% w/v, 40% w/v, 45% w/v, 50% w/v, 55% w/v, 60% w/v, 65% w/v, 70% w/v, 75% w/v, 80% w/v, 85% w/v, 90% w/v, 95% w/v, or 99% w/v polyacrylamide. In one embodiment, an N-dihyxylacrylamide gel includes 0 mM, 1 mM, 2 mM, 3 mM, 4 mM, or 5 mM ammonium persulfate. In another embodiments, an N-dihyxylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of ammonium persulfate. In one embodiment, an N-dihyxylacrylamide gel includes 0 mM, 1 mM, 2 mM, 3 mM, 4 mM, or 5 mM N'-methylenebis(acrylamide). In another embodiment, an N-dihyxylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of N'-methylenebis(acrylamide). In one embodiment, an N-dihyxylacrylamide gel includes 0 mM, 1 mM, 2 mM, 3 mM, 4 mM, or 5 mM N,N,N',N'-tetramethylethylenediamine. In another embodiment, an N-dihyxylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, or any range or subrange there between of N,N,N',N'-tetramethylethylenediamine. In one embodiment, an N-dihyxylacrylamide gel includes 0 mM, 1 mM, 2 mM, 3 mM, 4 mM, or 5 mM SDS. In one embodiment, an N-dihyxylacrylamide gel includes 0% w/v, 0.005% w/v, 0.01% w/v, 0.015% w/v, 0.02% w/v, 0.025%, w/v 0.03% w/v, 0.035% w/v, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.1% w/v, 0.2% w/v, 0.3% w/v, 0.4% w/v, 0.5% w/v, 0.6% w/v, 0.7% w/v, 0.8% w/v, 0.9% w/v, 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 15-20% w/v, 20-30% w/v, 30-40% w/v, 40-50% w/v, 50-55% w/v, 55-60% w/v, 60-65% w/v, 65-70% w/v, 70-75% w/v, 75-80% w/v, 80-85% w/v, 85-90% w/v, 90-95% w/v, or 95-99% w/v or any range or subrange there between of SDS.

In some embodiments, one or more of the anatomical structure, the first anatomical structure, the second anatomical structure, the connective tissue, and the tubular structure comprise one or more of: FlexSolid, FlexiFil, Makerbot-brand flexible filament, NinjaFlex, SemiFlex, TrueFlex, FilaFlex, x60, Stratysis tango series filament, Formlabs-brand flexible filament, thermoplastic polyurethane (TPU) or other thermoplastic elastomer (TPE). These materials may be printed by fuse deposition modeling (FDM), fused filament fabrication (FFF), selective laser sintering (SLS), or any other method known in the art.

In some embodiments, one or more of the anatomical structure, the first anatomical structure, the second anatomical structure, the connective tissue and the tubular structure are described by the amount of water present in its components. In some embodiments, the amount of water included is at least 40%. In some embodiments, the amount of water included is at least 50%. In some embodiments, the amount of water included is at least 60%. In some embodiments, the amount of water included is about 60% to about 70%. In one embodiment, the amount of water is 60%, 61%, 62%, 63%, 64%, 65%, 66%, 67%, 68%, 69%, or 70% or any range or subrange therein. In some embodiments, the amount of water included is about 70% to about 80%. In one embodiment the amount of water is 71%, 72%, 73%, 74%, 75%, 76%, 77%, 78%, 79%, or 80% or any range or subrange therein. In some embodiments that amount of water included is about 80% to about 90%. In one embodiment, the amount of water is 81%, 82%, 83%, 84%, 85%, 86%, 87%, 88%, 89%, or 90% or any range or subrange there. In some embodiments the amount of water is less than 90%.

In some embodiments, the connective tissues comprises or is formed of a gelatin or pectin-based composition. A gelatin-based synthetic connective tissue includes or is formed of 10-15% w/v gelatin, 45-55% v/v water, 115-120% w/v sugar (e.g., sucrose, but any type of sugar may be used, for example but without limitation, corn syrup, lecithin, cane sugar/syrup, sucrose, or dextrose), 50-55% v/v corn syrup, 1-2% w/v citric acid powder, and 0.25-0.75% v/v yellow dye. In some embodiments, the amount of gelatin is 5-10% w/v, 10-12% w/v, 12-14% w/v, 14-16% w/v, 16-18% w/v, 18-20% w/v, or any range or subrange there between. In some embodiments, the amount of gelatin is 13% w/v, 13.5% w/v, or 14% w/v. In some embodiments, the synthetic connective tissue includes 40-45% v/v, 45-50% v/v, 50-55% v/v, 55-60% v/v, or any range or subrange there between of water. In some embodiments, the synthetic connective tissue includes 49.5% v/v, 50% v/v, 50.5% v/v, 50.6% v/v, 50.7% v/v, 50.8% v/v, 50.9% v/v, 60% v/v, at least 50% v/v, or at least 50.5% v/v. In some embodiments, the synthetic connective tissue includes 110-112% w/v, 112-114%% v/v, 114-116% w/v, 116-118% w/v, 118-120% w/v, 120-122% w/v, or any range or subrange there between of sugar. In some embodiments, the synthetic connective tissue includes 116% w/v, 116.5% w/v, 117% w/v, 117.5% w/v, 117.6% w/v, 117.7% w/v, 117.8% w/v, 117.9% w/v, 118% w/v, at least 117% w/v, or at least 117.5% w/v sugar. In some embodiments, the synthetic connective tissue includes 45-50% v/v, 50-55% v/v, 55-60% v/v, or any range or subrange therebetween of corn syrup, lecithin, cane sugar/syrup, sucrose, or dextrose. In some embodiments, the synthetic connective tissue includes 50% v/v, 51% v/v, 52% v/v, 52.1% v/v, 52% v/v, 53% v/v, 54% v/v, 55% v/v, at least 50% v/v, or at least 52% v/v corn syrup. In some embodiments, the synthetic connective tissue includes 1% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, at least 1.0% w/v, or less than 1.0% w/v citric acid powder. In some embodiments, the synthetic connective tissue includes 0.25-0.35% v/v, 0.35-0.45% v/v, 0.45-0.55% v/v, 0.55-0.60% v/v, 0.60-0.65% v/v, 0.65-0.70% v/v, 0.70-0.75% v/v, or any range or subrange therebetween of yellow dye. In one embodiment, the amount of yellow dye is at least 0.5% v/v. In another embodiment, the amount of yellow dye is 0.6% v/v.

A pectin formulation may include 10-15% w/v pectin (e.g., high-methoxyl pectin, but any type of pectin is contemplated herein), 90-96% w/v sugar, 50-60% v/v corn syrup, 40-45% v/v water, 1-2% w/v citric acid powder, and 0.005-0.1% v/v yellow food coloring dye. In some embodiments, a synthetic connective tissue includes 8-10% w/v, 10-12% w/v, 12-14% w/v, 14-16% w/v, or any range or subrange therebetween of pectin. In one embodiment, the amount of pectin is at least 10% w/v. In one embodiment, the amount of pectin is at least 11% w/v. In one embodiment, the amount of pectin is about or substantially 11.5% w/v. In some embodiments, a synthetic connective tissue includes 88-90% w/v, 90-92% w/v, 92-94% w/v, 94-96% w/v, 96-98% w/v, or any range or subrange therebetween of sugar (e.g., sucrose, although any sugar is contemplated herein). In one embodiment, the amount of sugar is at least 80% w/v. In one embodiment, the amount of sugar is at least 90% w/v. In one embodiment, the amount of sugar is at least 94% w/v. In some embodiments, a synthetic connective tissue includes 48-50% v/v, 50-52% v/v, 52-54% v/v, 54-56% v/v, 56-58% v/v, or any range or subrange therebetween. In one embodiment, the amount of corn syrup is at least 50% v/v. In one embodiment, the amount of corn syrup is at least 55% v/v. In some embodiments, a synthetic connective tissue includes 36-38% v/v, 38-40% v/v, 40-42% v/v, 42-44% v/v, 44-46% v/v, or any range or subrange therebetween of water. In some embodiments, the amount water is at least 30%, 35%, or 40% v/v. In one embodiment, the amount of water is about or substantially 41% v/v. In some embodiments, the synthetic connective tissue includes 1% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, at least 1.0% w/v, or less than 1.0% w/v citric acid powder. In some embodiments, the synthetic connective tissue includes 0.25-0.35% v/v, 0.35-0.45% v/v, 0.45-0.55% v/v, 0.55-0.60% v/v, 0.60-0.65% v/v, 0.65-0.70% v/v, 0.70-0.75% v/v, or any range or subrange therebetween of yellow dye. In one embodiment, the amount of yellow dye is at least 0.5% v/v. In another embodiment, the amount of yellow dye is 0.6% v/v. In either gelatin or pectin formulas, 0.5% w/v to 50% milk may be used for opacity.

In some embodiments, one or more materials or compositions described herein may only be sold in limited colors. For example, x60 filament is only available in two colors: black and white. Unfortunately, accurate coloring of the materials is essential for proper identification of simulated organs and tissues in the system. Thus, in some embodiments, the filament may be melted down and additives added to the material to alter a color of the material, as described elsewhere herein. Further, additives may also be added to the material to alter its response to certain surgical equipment, for example electrosurgical tools or mechanical tools, including staplers, monopolar, bipolar, laser, harmonic, or ultrasonic instruments. Non-limiting examples of additives include: antioxidants, fillers/extenders, external lubricants, heat stabilizers, pigments, plasticizers, reinforcements, impact modifiers, internal lubricants, light stabilizers, and process aids. In some embodiments, the melted filament may be re-extruded to create a material with enhanced melting, ultrasonic, and dielectric properties. This process may be carried out for any of the filaments described herein.

The methods described herein and variations thereof can be embodied and/or implemented at least in part as a machine configured to receive a computer-readable medium storing computer-readable instructions. The instructions are preferably executed by computer-executable components preferably integrated with the system and one or more portions of the processor in the reservoir, the pump, and/or on the computing device communicatively coupled to the system. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "tubular structure" may include, and is contemplated to include, a plurality of tubular structures. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a system or composition.

As used herein, the term "comprising" or "comprises" is intended to mean that the systems, compositions, and methods include the recited elements, and may additionally include any other elements. "Consisting essentially of" shall mean that the systems, compositions, and methods include the recited elements and exclude other elements of essential significance to the combination for the stated purpose. Thus, a system, composition, or method consisting essentially of the elements as defined herein would not exclude other materials, features, or steps that do not materially affect the basic and novel characteristic(s) of the claimed disclosure. "Consisting of" shall mean that the systems, compositions, and methods include the recited elements and exclude anything more than a trivial or inconsequential element or step. Embodiments defined by each of these transitional terms are within the scope of this disclosure.

Example 1—General Manufacture

Most current physical surgery simulators depend on traditional manufacturing processes to create organs or tissues made from materials that have been manufactured on a large-scale for decades. The presently disclosed models are unique due to their composition as well as the realistic anatomy. Therefore, a different approach to manufacturing these models is required.

Patient Tissue Scanning

First, data from CT and/or MRI scans, or through other imaging means as described above, are obtained and then used to make a mold of a specific patient's tissue. The quality of the scans affects how accurately the data is extrapolated. For example, low-resolution scans will require more guess-work in the extrapolation of data. However, higher-resolution scans will allow for increased accuracy in recreating the patient's individual anatomy. The data extracted is manipulated by a series of processes including making the surfaces normal to one another, smoothing, modifying the geometry (includes smoothing operations), and reducing the number of faces. The mold is cut into any polyhedral geometry.

Milling

In some embodiments, the mold is created through a milling process. The individual polyhedra identified in the design process is then output to a computer numerical control (CNC) or analog mill. The then fabricated pieces are assembled with a mounting mechanism such as dowels, bolts, screws or chemical adhesive (such as glue). Pegs are incorporated into the design and milled out of the stock material. This ensures that the different parts of the mold are properly lined up or aligned.

Post-processing of the mold may depend on the material. Acceptable non-limiting materials for milling a mold include metal, plastic, wax, polystyrene, ceramic, and wood. For some materials, additional physical smoothing may be required and application of a polymeric coating such as polyurethane or polyacrylic creates a barrier between the metal and precursor solution. Wax may require additional smoothing by heating the mold to a specific temperature and using a curved surface to physically smooth one or more surfaces of the mold. If the mold is made of wax, placing boiling water in the mold to smooth the imperfections is commonly implemented but other methods may also be used.

Holes are drilled into the mold before preparation of the tissues begins. The holes are of any anatomical size or shape that is appropriate for that tissue. The pre-fabricated vessels (e.g., open-ended, blunt, closed-loop, or open-loop) are positioned in the holes such that they are snug enough that the precursor solution will not leak through. The hollow channels for the vessels can be drilled straight through a section of bulk material, be encapsulated between several polyhedra, or a combination of both.

Additionally, at least one hole is created in the mold for pouring of the pre-cursor solution. This hole is then covered or left uncovered during the material synthesis. Small air holes may also be drilled.

A gasket is required for a sealed mold. The gasket is implemented with any type of mold including milling, 3D printing, or vacuum forming. The gasket is typically laser-cut or manually cut. The interior of the gasket reflects the natural contour of the organ as determined from the CT, MRI, or other imaging data. The gasket is held into place by making it large enough such that the dowels, screws, bolts, or pegs pass through it and hold it into place.

3D Printing

In some embodiments, the mold is 3D printed. Any material could potentially be used for the 3D printing of the mold including, but not limited to, wax, wood, acrylonitrile butadiene styrene (ABS), polylactic acid (PLA), polyethylene terepthalate (PET), polyethylene terepthalate glycol (PETG), nylon, TPE (thermoplastic elastomers), TPU (thermoplastic polyurethane), high-impact polystyrene (HIPS), polyvinyl alcohol (PVA), metal, carbon fiber, lignin, polycarbonate (PC), polyethylene co-trimethylene terepthalate (PETT), acrylonitrile styrene acrylate (ASA), polypropylene (PP), polyoxymethylene (POM/acetal/polyacetal), polymethylmethacrylate (PMMA), sandstone, polycarbonate (PC), polycarbonate acrylonitrile butadiene styrene (PC-ABS), magnetic, nGen (Amphora AM3300), thermoplastic copolyester (TPC), poro-lay, and flexible polyester (FPE).

Pegs, or another aligning means, are included into the design of the mold to allow different parts of the mold to be aligned properly.

Vacuum Forming

Figures 18A, 18B, 18C:
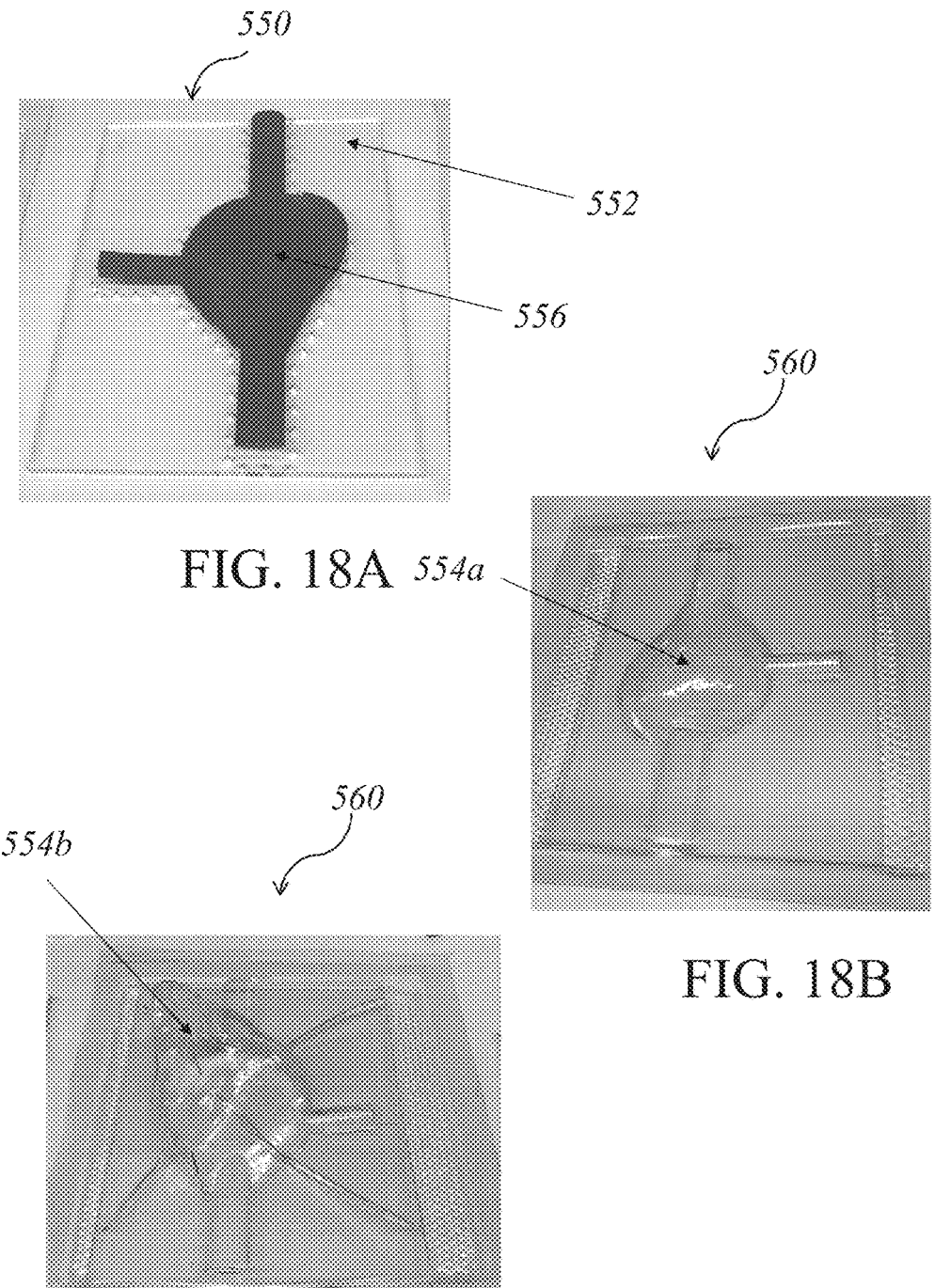
FIG. 18A illustrates a positive mold for production of an anatomical structure.
FIG. 18B illustrates a first half of a negative mold for production of an anatomical structure.
FIG. 18C illustrates a second half of a negative mold for production of an anatomical structure.
Figure 19A:
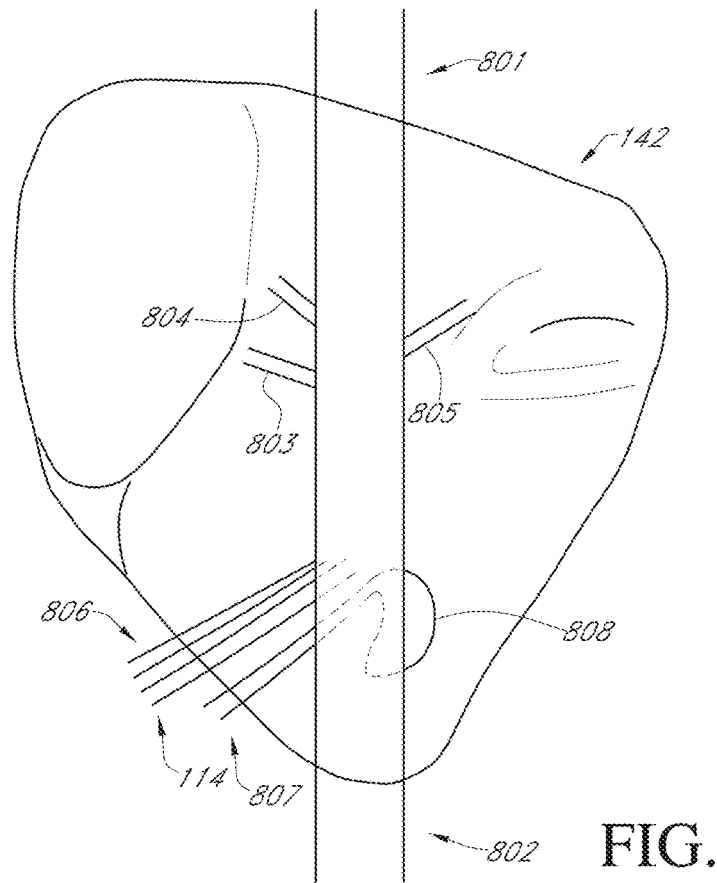
FIG. 19A illustrates a left side view of one embodiment of an anatomical structure for use in a veno-venous bypass procedure.
Figure 19B:
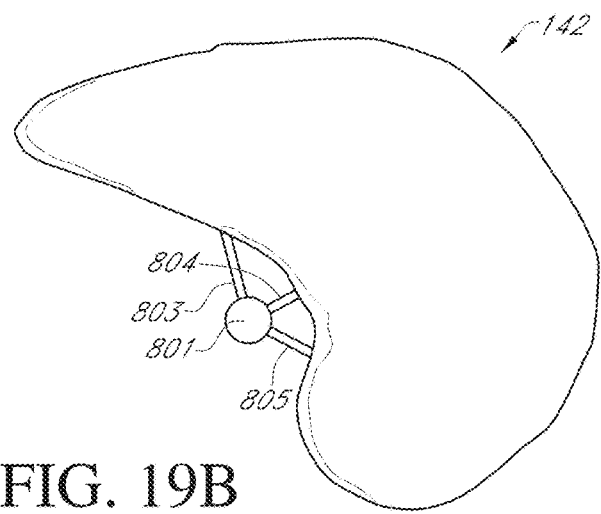
FIG. 19B illustrates a proximal view of one embodiment of an anatomical structure for use in a veno-venous bypass procedure.
Figure 19C:
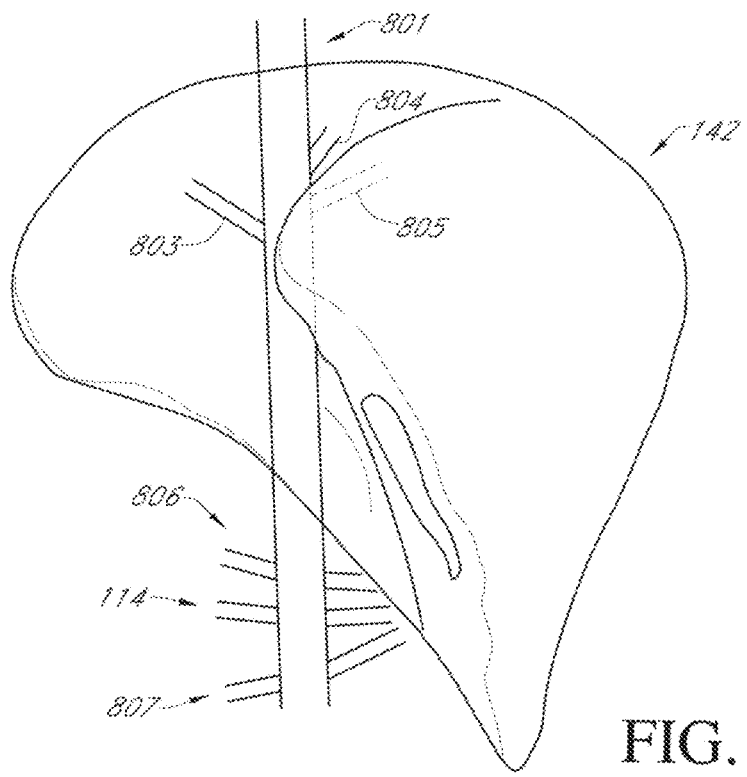
FIG. 19C illustrates a dorsal view of one embodiment of an anatomical structure for use in a veno-venous bypass procedure.
Figure 19D:
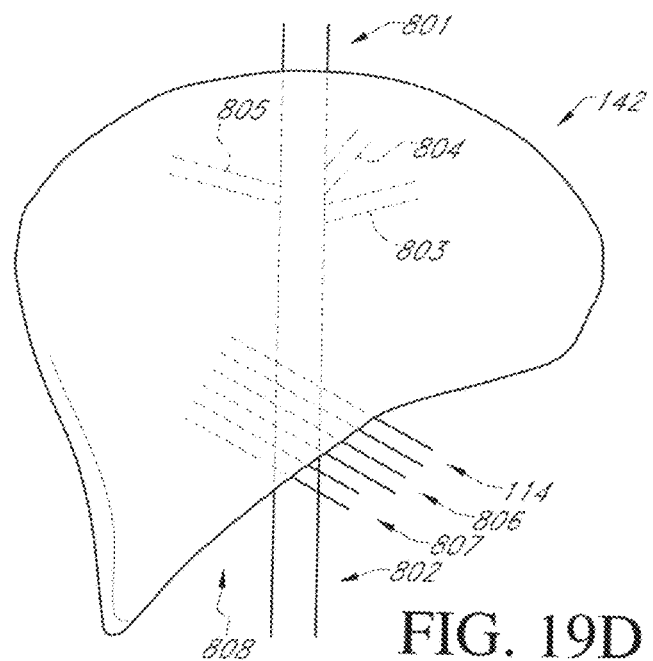
FIG. 19D illustrates a ventral view of one embodiment of an anatomical structure for use in a veno-venous bypass procedure.

In some embodiments, as shown in FIGS. 18A-18C, the mold 550 includes a positive mold 556 (e.g., a 3D printed anatomical structure) coupled to a plate 552 (e.g., acrylic). In some embodiments, the negative mold 554 is formed of two halves 554a, 554b (e.g., a first half is shown in FIG. 18B and a second half is shown in FIG. 18C); in other embodiments, the negative mold is monolithic or formed of a plurality of sections. To form the negative mold 554, a plastic sheet (e.g., polypropylene, PET or PETG) is partially melted, for example by the application of heat, and the positive mold 556, or a cross-section of the positive mold, is positioned below the partially melted plastic sheet. Vacuum suction is applied to a bottom surface of the plate 552 coupled to the positive mold 556 causing the negative mold 554 to form around the positive mold 556. This vacuum suction creates an indentation, groove, impression, or depression 554 in the negative mold 554 that resembles at least one side or surface of the positive mold 556. These steps may be repeated to form a second negative mold, for example as shown in FIG. 18C, in embodiments where the negative mold is formed of two halves or a plurality of sections. In other embodiments where the negative mold is monolithic, two or more plastic sheets may be heated and/or vacuum sealed around a removable positive mold. In some such embodiments, the negative mold includes holes, apertures, or cavities therein in which tubular structures will be inserted or threaded through at a later time point. The deformed plastic sheet may be trimmed around the indentation left by the positive mold to form the negative mold or one half or section of the negative mold. In such embodiments where the negative mold is formed of two halves or a plurality of sections, the tubular structures (e.g., vessels) are positioned between the two halves or the plurality of sections before sealing the two halves or the plurality of sections together to form the negative mold.

The two halves or the plurality of sections are sealed together using a sealant. Exemplary, non-limiting examples of sealants include silicone based sealants, epoxy, or superglue-like sealants. Once the two halves or plurality of sections are sealed together, compositions used to form the simulated anatomical structures are poured into the negative mold using an aperture or hole in the negative mold. In some embodiments, the negative mold further includes a second aperture or hole through which air in the negative mold can escape as the composition(s) are poured into or added into the negative mold. After the simulated anatomical structure solidifies or polymerizes, the negative mold is removed.

In some embodiments, the negative mold further includes a gasket. The gasket is positioned between the halves or sections of the negative mold. In some embodiments, the gasket comprises or is formed of a rubbery material (e.g., rubber, silicone, a material softer than the material of the negative mold); in other embodiments, the gasket comprises or is formed of a hard plastic (e.g., acrylic). Variation of the negative mold may include a custom 3D printed ring comprising or formed of any of the thermoplastic materials listed elsewhere herein. The ring is fabricated to account for a gap that typically occurs between the halves or sections of the negative mold. The interior of the ring reflects the natural contour of the positive mold or simulated anatomical structure as determined from the CT, MRI, or other imaging data. The ring is configured to fit snugly at the junctions of each half or section of the negative mold. Any combination of these features of a negative mold may be used together. Materials that could be vacuum formed include any thermoplastic material including, but not limited to, HIPS, ABS, PETG, polystyrene, acrylic, polycarbonate, HDPE, LDPE, PMMA, polypropylene or polyvinyl chloride.

Mold Uses

After the mold is created, the tissues for simulation are fabricated. First, the vessels are carefully fed through the vessel-holes or physically placed into specific indentations intended for vessels such as those in FIG. 18B. Then, the polyhedra (parts?) of the mold are mounted to one another by dowels, bolts, screws, chemical adhesive, or other bonding means. Next, the prepared pre-cursor solution is poured into the mold. This hole may or may not be closed up to create a better-controlled environment for the polymer synthesis. The organ is then carefully removed from the mold.

Example 2—Simulation of Liver for Liver Transplant-Related Procedures

The liver simulator is comprised of several components, and one embodiment is illustrated in FIGS. 19A-D in left side view, proximal view, dorsal view, and ventral view: the liver 142, vessels (superior vena cava 801, inferior vena cava 802, left hepatic vein 803, middle hepatic vein 804, right hepatic vein 805, hepatic portal vein 114 and hepatic artery 806 with at least three of their corresponding divisions each), and gallbladder 808 connected with common bile duct 807. The simulator can also comprise connective tissue connecting or covering the gall bladder and the liver, that is, one or more of the reticulin, adventia, and the serosa. The liver simulator can also include the small intestine, depending on the precise operative steps to be trained. Additional possible components are illustrated in FIG. 2 and FIG. 15: synthetic blood 430, external reservoir 116, pump 118, and blood loss detection through computing device 20. The purpose of this simulator is to allow the users to practice handling techniques of the organ harvest as well as proper bypass techniques.

To faithfully recreate the VVB procedure, the portal, arterial and hepatic venous systems are inter-connected inside the liver parenchyma 146, thus allowing pump pressure gradient driven artificial blood 430 to flow from hepatic vena cava 801 to superior hepatic vena cava 802 and from portal vein 114 and hepatic artery 806. In some embodiments, artificial blood flows from three branches of the portal vein and/or hepatic artery into the hepatic veins and ultimately into the superior hepatic vena cava 802, although less branches can be utilized to simplify the procedure. Of note, preferably the inflow via hepatic artery is pulsatile, but the portal limb of inflow is not as it is connected through the pressure reducing pulse dumping regulator. This imitates the natural blood circulation of the liver. For the purpose of simulation, the inferior hepatic vena cava 801, portal vein 114, and hepatic artery 806 vascular loops on one end, and superior hepatic vena cava 802 on the other, are connected to each other via pump 118 to allow for uninterrupted circulation.

Veno-Venous Bypass (VVB) Procedure

Because of the unique characteristics of the presently disclosed surgical simulation systems and methods, surgical students can gain realistic experience in a procedure used in liver transplantation, the veno-venous bypass. See, for example Fonouni et al., HBP (Oxford), 2008, 10(3):196-203 discussing the use of the procedure. During liver transplantation several large blood vessels need to be clamped in order to complete the operation. This clamping can result in lowered patient blood pressure and lowered blood flow to vital organs. To address these issues, veno-venous bypass is used to establish circulation outside the body, through a pump, in a manner that avoids the liver circulation and the clamped vessels. There are a number of stated advantages for the use of VVB beyond blood pressure support and better perfusion of vital organs such as decreased need for blood transfusions, a longer time for the surgeon to perform those aspects of the operation that occur with the liver removed from the patient, and improved short term survival (Fonouni et al. 2008). The simulation systems described herein contemplate a VVB set up of a femoral/portal-subclavian loop, although the simulation can be adapted to support any contemplated VVB approach.

The presently disclosed surgical simulation system is used in a training exercise for VVB as follows. After simulated trial of clamping of the superior hepatic vena cava and a simulated fall in vital signs, the decision of carrying out the VVB is announced. The surgeon clamps and cuts the elements of the portal triad (i.e., portal vein, hepatic artery, and common bile duct), and then either fully cuts both the inferior and superior hepatic segments of the vena cava, or partially clamps the segment of vena cava located behind the liver that includes the confluence of all three hepatic veins. With the blood flow stopped, the liver is then explanted (removed). At the same time, another user being trained as a member of the surgical and/or anesthesia team establishes simulated femoral and subclavian venous access. The training transplant surgeon also cannulates the stump of the portal vein, and the training perfusionist team connects VVB machine to the three established connection points: simulated femoral vein, simulated portal vein, and simulated subclavian artery. VVB commences with femoral and portal loops on one end and subclavian on the other, thus causing the artificial blood to bypass the liver site. Of note, the femoral vein loop is now connected to the Y-branch of the portal stump loop, while the hepatic Y-branch is clamped. The just explanted simulated liver is reintroduced as "donor" liver and is reconnected to the "recipient" vascularity.

The "recipient's" portal vein and hepatic artery stumps are anastomosed (reconnected) end-to-end directly to the "donor" liver portal vein and hepatic artery, and the common bile duct is sewn to the loop of small intestine (or this part of the transplant procedure is simply verbalized if the small intestine is not present in the simulation system being used). The restoration of the liver caval flow (e.g. reestablishing blood flow from the clamped vena cava) could be carried out in one of the three possible ways depending on the surgeon's choice or the goals of the exercise: 1) "donor" and "recipient" inferior and superior hepatic segments are anastomosed directly end-to-end; 2) "donor" liver hepatic veins are sewn to the joint cuff of the remains of the "recipient" hepatic veins, in so called "piggy-back technique"; or 3) recipient and "donor" caval veins are sewn together "side-to-side." In this way, a full liver transplantation operation can be simulated using the system described herein. Notably, the simulation run could be stopped at any point depending on the need for instruction, direction, or to alter the scenario.

In some embodiments, a basic or simplified simulated VVB system includes an anatomical structure (e.g., simulated liver), and a network of tubular structures comprising, for example a simulated superior vena cava, a simulated inferior vena cava, and a simulated portal vein. In some embodiments, an advanced or complex simulated VVB system includes a first anatomical structure (e.g., simulated liver), a second anatomical structure (e.g., simulated gall bladder), and a network of tubular structures comprising, for example a simulated superior vena cava, a simulated inferior vena cava, a simulated left hepatic vein, a simulated middle hepatic vein, a simulated right hepatic vein, a simulated hepatic artery, a simulated portal vein, and a simulated common bile duct.

Liver Donor Liver Harvesting

The liver simulation system can also be used to train users in the harvesting of liver from a liver donor. The simulation can be utilized to mimic operative procedures for a live donor as well as operative procedures for cadaveric donation. The liver inside the simulated abdomen is perfused via portal vein, hepatic artery into the hepatic veins, and vena cava. The intraoperative ultrasound is performed visualizing the anatomically and correctly reproduced interconnected branches of the portal vein, hepatic artery, and hepatic veins. The recipient liver can be further simulated using a simulated gall bladder and bile duct. It can also comprise associated connective tissue such as the reticulin, which covers the liver, the adventia, connective tissue that attaches the gall bladder to the liver, and/or serosa, connective tissue that covers the gall bladder where it is not attached to the liver. The extent of harvested portion of the "donor" liver is decided upon based on the simulation scenario. The resection procedure is performed using a combination of the electrosurgical sharp and blunt dissection. The harvested portion of the liver with its vascularity is explanted (removed) and the "hemostasis" of the remaining organ is carefully checked.

Composition of Liver

The vessels may be composed of any of the materials described elsewhere herein. The liver and contained interconnected tubular structures, representing portal vein, hepatic artery, and biliary and hepatic/venous caval systems, are amenable to direct imaging with clinical grade intraoperative ultrasound or any other imaging method known in the art (e.g., applying light and/or sound to an exterior surface to visualize internal vascular structures), as well the dissection by any of the clinical grade electrosurgical instrumentation. Because of these novel characteristics of the present simulation system, its use is a close match to the procedures involved in actual liver donation. Possible training includes simulation of establishing VVB in the recipient, removal of the diseased liver, and installation of the "donor" liver. In a separate training session, the simulation system can provide training on removal of the donor liver from either a live or recently deceased donor.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processor on the computing device. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A synthetic surgical simulation system comprising:
   an anatomical structure comprising a gelatin hydrogel;
   a connective tissue comprising an alginate hydrogel comprising 0.25% to 10% w/v sodium alginate and 0.01-2 M CaCl2 in water; and
   a tubular structure at least partially embedded in one or more of the anatomical structure and the connective tissue structure,
   wherein the anatomical structure and the connective tissue respond to an application of energy emitted by an electrosurgical tool by at least partially vaporizing, burning, and cutting.

2. The system of claim 1, wherein the tubular structure is a network wherein the network extends from the anatomical structure and is coupled to a reservoir, and wherein the reservoir monitors an amount of blood loss during a medical training session.

3. The system of claim 2, further comprising a pump coupled to the reservoir, wherein the pump pumps a fluid from the reservoir through the network of tubular structures.

4. The system of claim 3, wherein the fluid is pumped in a pulsatile manner.

5. The system of claim 1, wherein a three-dimensional shape of the anatomical structure is based on one or more of: a computerized tomography scan, a magnetic resonance imaging scan, and a magnetic resonance elastography scan of a body portion of a patient.

6. The system of claim 1, wherein one or more of: the gelatin hydrogel and the alginate hydrogel comprise at least 10% water.

7. The system of claim 1, wherein the anatomical structure further comprises one or more sugars.

8. The system of claim 1, wherein the anatomical structure further comprises one or more of: sucrose, corn syrup, citric acid, and a combination thereof.

9. The system of claim 1, wherein the system further comprises:
   a three-dimensional mold of the anatomical structure; and
   a negative mold comprising a partially melted sheet, wherein the three-dimensional mold is positioned adjacent to the negative mold, and wherein vacuum suction is applied to the three-dimensional mold to draw the negative mold at least partially around the three-dimensional mold so that the negative mold is formed to receive the gelatin hydrogel therein to form the anatomical structure.

10. The system of claim 1, wherein the anatomical structure is one of: a synthetic adrenal gland, a synthetic kidney, and a synthetic lymphatic tissue.

11. The system of claim 1, wherein the connective tissue comprises a top layer and a bottom layer, wherein the top layer comprises the alginate hydrogel, and the bottom layer comprises a second gelatin hydrogel.

12. The system of claim 1, wherein the connective tissue comprises a top layer, a middle layer, and a bottom layer, wherein the top layer and the bottom layer comprise the alginate hydrogel, and the middle layer comprises a second gelatin hydrogel.

13. The system of claim 12, wherein the top layer and the bottom layer at least partially encapsulate the middle layer.

14. A synthetic surgical simulation system comprising:
   a first anatomical structure comprising a gelatin hydrogel, wherein the first anatomical structure is configured to at least partially vaporize, burn, and cut in response to an application of energy emitted by an electrosurgical tool;
   a second anatomical structure;
   a connective tissue coupling the first anatomical structure to the second anatomical structure; and
   a tubular structure at least partially embedded in one or more of the first anatomical structure, the second anatomical structure, and the connective tissue.

15. The system of claim 14, wherein the first anatomical structure is a liver and the second anatomical structure is a gall bladder and the connective tissue is one or more of a synthetic reticulin, a synthetic adventia, and a synthetic serosa.

16. The system of claim 14, wherein the tubular structure comprises one or more of: a synthetic superior vena cava, a synthetic inferior vena cava, a synthetic left hepatic vein, a synthetic middle hepatic vein, a synthetic right hepatic vein, a synthetic hepatic artery, a synthetic hepatic portal vein, and a synthetic common bile duct.

17. A synthetic surgical simulation system comprising:
   a first anatomical structure comprising a gelatin hydrogel;
   a second anatomical structure;
   a connective tissue comprising an alginate hydrogel comprising 0.25% to 10% w/v sodium alginate and 0.01-2 M CaCl2 in water,
      wherein the connective tissue is configured to couple the first anatomical structure to the second anatomical structure, and
      wherein the first anatomical structure and the connective tissue are further configured to at least partially vaporize, cut, and burn in response to an application of energy emitted by an electrosurgical tool; and
   a network of tubular structures comprising:
      a first portion at least partially embedded in the first anatomical structure,
      a second portion at least partially embedded in the second anatomical structure, and a third portion at least partially embedded in the connective tissue, wherein the first portion, the second portion, and the third portion of the network of tubular structures are interconnected to further couple the first anatomical structure, the second anatomical structure, and the connective tissue together.

18. The system of claim 17, wherein the first anatomical structure is a synthetic spleen, the second anatomical structure is a synthetic stomach, and the connective tissue is a synthetic splenogastric ligament.

19. The system of claim 17, wherein the first anatomical structure is a synthetic spleen, the second anatomical structure is a synthetic pancreas, and the connective tissue is a synthetic splenic-pancreatic ligament.

20. The system of claim 17, wherein the first anatomical structure is a synthetic spleen and the second anatomical structure is a synthetic colon, and the connective tissue is a synthetic splenocolic ligament.

* * * * *